(12) United States Patent
Thomason et al.

(10) Patent No.: US 8,486,030 B2
(45) Date of Patent: Jul. 16, 2013

(54) HAND HELD SKIN TREATMENT SPRAY SYSTEM WITH PROPORTIONAL AIR AND LIQUID CONTROL

(75) Inventors: Scott Thomason, Macedonia, OH (US); Steven C. Cooper, Athens, GA (US)

(73) Assignee: Sunless, Inc., Macedonia, OH (US)

( * ) Notice: Subject to any disclaimer, the term of this patent is extended or adjusted under 35 U.S.C. 154(b) by 178 days.

(21) Appl. No.: 12/910,754

(22) Filed: Oct. 22, 2010

(65) Prior Publication Data

US 2011/0137268 A1    Jun. 9, 2011

Related U.S. Application Data

(60) Provisional application No. 61/266,810, filed on Dec. 4, 2009.

(51) Int. Cl.
*A61F 7/00* (2006.01)
*B05B 1/24* (2006.01)

(52) U.S. Cl.
USPC .......................................... 604/291; 239/133

(58) Field of Classification Search
USPC .......................................................... 604/291
See application file for complete search history.

(56) References Cited

U.S. PATENT DOCUMENTS

| | | | | |
|---|---|---|---|---|
| 1,586,009 A | * | 5/1926 | Shelburne | 239/133 |
| 1,982,509 A | * | 11/1934 | Frank | 604/289 |
| 2,139,133 A | * | 12/1938 | Paasche | 239/298 |
| 2,267,264 A | * | 12/1941 | Bland | 392/494 |
| 2,284,235 A | * | 5/1942 | Ronzi | 128/200.14 |
| 2,401,504 A | * | 6/1946 | Paasche | 239/133 |
| 3,057,558 A | * | 10/1962 | Verba et al. | 239/700 |
| 3,344,992 A | * | 10/1967 | Norris | 239/8 |
| 3,437,791 A | * | 4/1969 | Gardner | 392/476 |
| 3,662,407 A | * | 5/1972 | Colucci | 4/420.2 |
| 3,721,250 A | * | 3/1973 | Walter et al. | 132/112 |
| 3,770,201 A | * | 11/1973 | Sanders | 239/135 |
| 3,780,943 A | * | 12/1973 | Lilja | 239/8 |

(Continued)

FOREIGN PATENT DOCUMENTS

| | | |
|---|---|---|
| DE | 3540990 A1 | 5/1987 |
| DE | 3720938 A1 | 1/1989 |

(Continued)

OTHER PUBLICATIONS

Tanning Essentials, Manual: Classic Tanning Essentials Spray Tan System, date unknown (8 pages).

(Continued)

*Primary Examiner* — Melanie Hand
*Assistant Examiner* — Paula Craig
(74) *Attorney, Agent, or Firm* — Gardere Wynne Sewell LLP; Andre M. Szuwalski

(57) ABSTRACT

A spray nozzle system includes separate air outlets to deliver one or more streams of supplemental warming or drying air. The air may be applied while spray is emitted from the nozzle to increase the spray cloud temperature, or may be applied for warming or drying before or after the spray application, with the spray turned off. In the case of air-atomizing nozzles, the air is delivered through low pressure ports separately from the atomizing or pattern shaping air to minimize the expansion cooling effect. In another implementation, the air is redirected from the nozzle using a control valve which proportions the amount of airflow directed for atomization, pattern shaping and drying.

30 Claims, 17 Drawing Sheets

U.S. PATENT DOCUMENTS

| | | | |
|---|---|---|---|
| 3,854,489 A | 12/1974 | Doyle et al. | |
| 3,905,379 A * | 9/1975 | Churas et al. | 132/272 |
| 3,947,659 A * | 3/1976 | Ono | 392/404 |
| 4,114,022 A | 9/1978 | Braulke, III | |
| 4,149,536 A * | 4/1979 | Villard | 604/291 |
| 4,166,473 A * | 9/1979 | Bauer et al. | 132/272 |
| 4,300,556 A * | 11/1981 | Ochi et al. | 604/291 |
| 4,394,967 A | 7/1983 | Amiaut | |
| 4,523,080 A | 6/1985 | Bolton | |
| 4,597,757 A * | 7/1986 | Ruderian | 604/291 |
| 4,605,019 A * | 8/1986 | Reynolds et al. | 132/272 |
| 4,761,837 A * | 8/1988 | Takeda | 4/443 |
| 4,836,137 A | 6/1989 | Heine et al. | |
| 4,915,303 A * | 4/1990 | Hufgard | 239/300 |
| 5,038,769 A | 8/1991 | Krauser | |
| 5,074,322 A | 12/1991 | Jaw | |
| 5,078,322 A * | 1/1992 | Torntore | 239/289 |
| 5,102,051 A * | 4/1992 | Smith et al. | 239/297 |
| 5,241,974 A * | 9/1993 | Tsai | 132/272 |
| 5,261,427 A * | 11/1993 | Dolev | 132/200 |
| 5,339,540 A * | 8/1994 | Edwards | 34/97 |
| 5,387,200 A | 2/1995 | Kronstadt | |
| 5,520,519 A * | 5/1996 | Birkeland | 417/63 |
| 5,558,276 A | 9/1996 | Barrett et al. | |
| 5,603,341 A | 2/1997 | Johnson | |
| 5,642,570 A * | 7/1997 | Lee | 34/98 |
| 5,971,298 A * | 10/1999 | Millan et al. | 239/290 |
| 5,991,937 A | 11/1999 | Safara | |
| 6,106,547 A * | 8/2000 | Huei-Jung | 607/96 |
| 6,302,122 B1 | 10/2001 | Parker et al. | |
| 6,554,208 B1 | 4/2003 | Venuto, Sr. | |
| 6,923,794 B2 * | 8/2005 | Ohmura | 604/291 |
| 6,973,679 B1 * | 12/2005 | Schad | 4/420.4 |
| 7,041,089 B2 | 5/2006 | Laughlin | |
| 7,132,010 B2 | 11/2006 | Carlsson | |
| 7,387,684 B2 | 6/2008 | Cooper et al. | |
| 7,569,037 B1 | 8/2009 | Spivak | |
| 7,772,526 B2 * | 8/2010 | Chuong | 219/385 |
| 2004/0156793 A1 * | 8/2004 | Golden et al. | 424/47 |
| 2004/0228810 A1 * | 11/2004 | Hamson et al. | 424/47 |
| 2005/0242207 A1 * | 11/2005 | Tejeda | 239/346 |
| 2005/0279865 A1 | 12/2005 | Thomason et al. | |
| 2005/0281957 A1 | 12/2005 | Cooper et al. | |
| 2006/0032946 A1 * | 2/2006 | Cooper et al. | 239/532 |
| 2006/0102096 A1 * | 5/2006 | Cho | 119/671 |
| 2006/0214027 A1 | 9/2006 | Micheli | |
| 2007/0169261 A1 | 7/2007 | Smith et al. | |
| 2007/0197982 A1 | 8/2007 | Thomason et al. | |
| 2008/0071332 A1 | 3/2008 | Nelson et al. | |
| 2008/0237522 A1 | 10/2008 | Morris | |
| 2009/0114236 A1 * | 5/2009 | Mehta | 132/200 |
| 2009/0130044 A1 * | 5/2009 | Choi et al. | 424/70.1 |
| 2009/0272316 A1 | 11/2009 | Arnaud et al. | |
| 2010/0266776 A1 * | 10/2010 | Cooper et al. | 427/372.2 |
| 2011/0060195 A1 * | 3/2011 | De Noray et al. | 600/249 |
| 2011/0133001 A1 | 6/2011 | Cooper et al. | |
| 2011/0133004 A1 | 6/2011 | Thomason et al. | |
| 2011/0202019 A1 | 8/2011 | Cooper et al. | |
| 2011/0259974 A1 | 10/2011 | Cooper et al. | |

FOREIGN PATENT DOCUMENTS

| | | |
|---|---|---|
| EP | 0359943 A2 | 3/1990 |
| JP | 2000135111 A | 5/2000 |
| WO | WO-2004033107 A2 | 4/2004 |
| WO | WO-2004069322 A1 | 8/2004 |
| WO | WO-2010012903 A1 | 2/2010 |
| WO | WO-2010123922 A1 | 10/2010 |

OTHER PUBLICATIONS

International Search Report and Written Opinion, mailed Feb. 1, 2011, for PCT/US2010/058998 (15 pages).

EPO Supplemental Search Report and Written Opinion for EP10835237.8 mailed Apr. 17, 2013 (8 pages).

* cited by examiner

HAND HELD SKIN TREATMENT SPRAY SYSTEM WITH PROPORTIONAL AIR AND LIQUID CONTROL

PRIORITY CLAIM

This application claims priority from U.S. Provisional Application for Patent No. 61/266,810, filed Dec. 4, 2009, the disclosure of which is hereby incorporated by reference.

BACKGROUND

Spray devices for the application of liquids onto human skin and hair are well known. Sprays are used for many types of medicines, skin treatments, hair treatments, deodorants, lotions, and cosmetic agents. Specialized hand-held and automated spray systems have recently been introduced in tanning salons and spa treatment centers to apply sunless tanning compounds and skin care formulas, such as moisturizers, anti-aging treatments, and exfoliants. The spray solution used for sunless tanning is generally a water-based mixture of DHA (dihydroxyacetone) and/or erythrulose and various other skin care ingredients such as aloe vera. Often a cosmetic bronzer is added along with pleasant scents and ingredients to enhance tanning performance, such as formulations to balance skin ph. For best results, the spraying of the solution utilizes a finely atomized spray (mist), as opposed to the use of a spray stream or large spray droplets, because the mist of solution provides for even coverage and reduces the risk of streaking or running of the spray deposit.

The skin treatment spray process has inherently been a cold, uncomfortable experience for the recipient as nozzle expansion effects significantly cool the air and liquid in the spray cloud during application to the skin. Furthermore, cold skin is known to inhibit optimum absorption of the skin care ingredients. Temperatures of the spray cloud can be over 30 degrees (F) lower than human body temperature due to nozzle cooling and significantly cooler than ambient temperature (of the air or the liquid). Heating of the spray liquid or the atomization air has a negligible effect on increasing spray cloud temperature due to the rapid cooling produced as the spray jet expands when exiting the nozzle. This phenomenon is magnified when using air-atomizing nozzles; the type most desirable for producing a finely atomized spray mist.

In salons, customers disrobe for the spray treatment which lasts from 30 seconds to 5 minutes. Some treatments involve sequential spray regimens of alternate ingredients so the experience can be significantly longer. Thus, the length of time the customer is exposed to cold can be significant and may discourage the customer from obtaining the treatment in the first place or returning for an additional treatment at a later date.

After the spray treatment customers often use a towel to dry their skin. The action of toweling-off removes a significant quantity of the sprayed ingredients from the skin. The remaining ingredients may be redistributed, which can produce a splotchy appearance in the case of sunless tanning or other cosmetic treatments. If the customer opts not to use a towel, and instead simply dry off in the ambient air or from the cool air of air-atomizing nozzles, the surface of the skin can become sticky.

Many tanning salons providing the new sunless spray tanning service also have conventional UV lamp tanning beds. Customers have observed that application of sunless tanning solutions quickly after they use a UV tanning bed can result in a deeper and darker DHA tan. It is important to move from the UV tanning bed to receive a spray of sunless tanning solution as quickly as possible. It is also essential to remove all perspiration resulting from the UV treatment or the tan result can be uneven. The benefits of UV tanning coupled with a sunless tanning spray may be due to opening the pores of the skin and from more thoroughly and more deeply drying out of the top skin layer by the hot UV lamps. However, due to skin health concerns, many customers do not wish to use the UV beds and therefore cannot take advantage of this practice to enhance their sunless tan.

DHA tans the skin by reacting with proteins in the stratum corneum, the top protective skin layer composed of dead skin cells. It is known that only the uppermost dry layers of the stratum corneum will tan effectively with DHA or erythrulose. Very dry skin will pigment the darkest and layers containing surface moisture will not tan nearly as well. Skin care specialists suggest using a warm towel on the skin before application of spray treatments since warm skin may better absorb some ingredients. However, a skin surface that is too hot will perspire, thus reducing the effectiveness of the sprayed ingredients.

A need exists in the art to address the foregoing issues in connection with providing a better sunless tanning experience and result for the consumer.

Reference is further made to Venuto, U.S. Pat. No. 6,554,208 (the disclosure of which is hereby incorporated by reference) which teaches a tanning spray booth implementation with a nozzle operable to both spray tanning solution and deliver drying air when not spraying.

Reference is also made to Safara, U.S. Pat. No. 5,991,937 (the disclosure of which is hereby incorporated by reference) which teaches a bidet sprayer implementation operable to both spray cleaning water streams and deliver drying air when not spraying.

SUMMARY

Embodiments disclosed herein propose the controlled application of warm dry air over the skin before, during and after applications of atomized (misted) sunless tanning sprays using a hand held spray type system. This controlled application enhances efficacy of the tanning compounds and results in a deeper tan color and a longer lasting tan. In addition, the mixing of heated dry air into the atomized spray cloud reduces the discomfort caused by the inherently cold spray stream. Furthermore, warm dry air, applied during and after short spray sequences enhances the spray uniformity result and produces a softer characteristic feel of the spray ingredients on the skin, while reducing complaints of "stickiness" or "tackiness" by the consumer. Deposition efficiency and uniformity of the tan result is improved since the towel dry step after the spray session is no longer necessary.

A spray nozzle system in a hand held spray format is presented for applying topical skin treatments, such as sunless tanning formulations, medicines, and lotions. Specifically, liquids or suspensions are applied to human skin using a hand held spray system which allows for controlled operation of a heated air system and an atomizing spray liquid dispensing system.

A spray nozzle system includes auxiliary air outlets positioned near the liquid spray outlet of the spray nozzle to deliver one or more streams of warming air for the purpose of drying the skin surface and mixing with the spray cloud so as to improve the comfort of the spraying experience. The drying air from the auxiliary ports may be applied while the spray cloud is emitted from the nozzle to increase the spray cloud temperature (and thus counteract the temperature drop caused by nozzle expansion effects), or may be applied before or after the spray application, with the spray turned off, to warm or dry the skin.

A heating source is provided to warm the air that is directed through one or more air outlets. In a preferred embodiment, a heating element is incorporated into the hand held sprayer. The heating element may be positioned at the air outlet or in the air conduit within the hand held spray device or in the air hose to the air outlets or at the air pump. In the case of air atomizing nozzles, the warming air is supplemental to the atomizing air at the nozzle and is delivered through low pressure outlets separate from the air emitted through the nozzle's atomizing and/or pattern shaping orifices to minimize the expansion cooling effect inherent with the spray nozzle ports.

In another embodiment, the heated airflow is redirected from the nozzle jets to one or more of the supplemental air outlets. In this embodiment, a control valve may be used to proportion the amount of airflow directed to the main atomizer air jets, the pattern shaping air jets and the supplemental air outlets for drying the skin.

The method of applying warm dry air between layered applications of atomized spray deposition has been found to make the experience of skin spray treatments much more comfortable as well as improve coating uniformity. In addition, this method provides an improved tack-free feel of the spray deposit on the skin both during and after the spray session. In the case of sunless tanning with active ingredients such as Erythrulose or DHA (dihydroxyacetone), the system provides for an improved tanning color and increased longevity of the tan.

In an embodiment, an apparatus comprises: a hand held spray member; a spray nozzle supported by the hand held spray member, the spray nozzle including a spray jet outlet adapted to spray a skin treatment liquid from the spray nozzle and produce a finely atomized spray cloud of the skin treatment liquid; a liquid valve supported by the hand held spray member, the liquid valve adapted to control flow of the skin treatment liquid to the nozzle jet outlet; a warm air outlet separate from the spray jet outlet, the warm air outlet adapted to deliver heated air in a warm air stream directed to mix with and warm the finely atomized spray cloud produced by the spray jet outlet; an air valve supported by the hand held spray member, the air valve adapted to control flow of air to the warm air outlet; and a controller adapted to proportionally control actuation of the liquid valve and air valve in response to a trigger actuation.

BRIEF DESCRIPTION OF THE DRAWINGS

A more complete understanding of the invention may be obtained by reference to the following drawings.

DETAILED DESCRIPTION OF THE DRAWINGS

Figure 1:
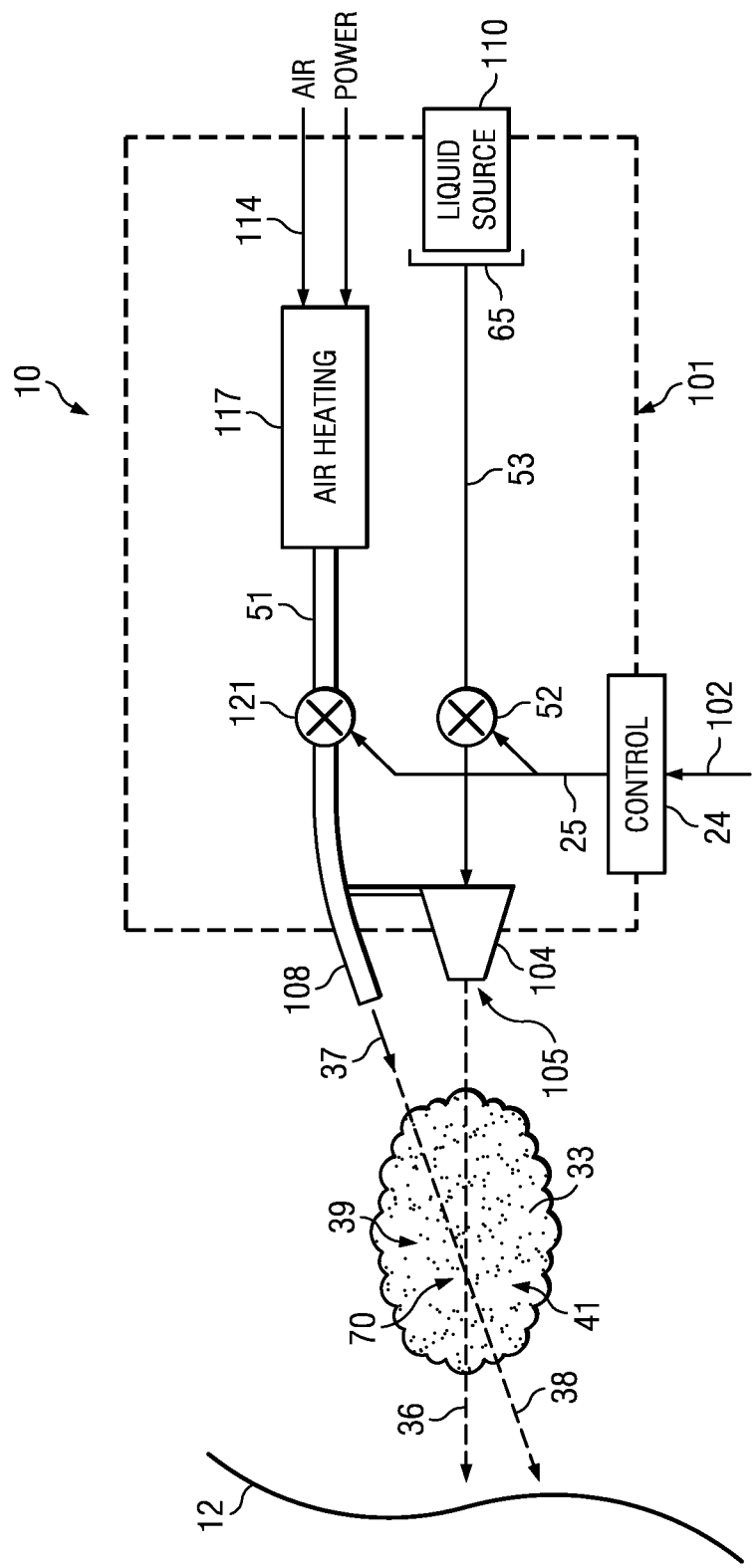
FIG. 1 schematically illustrates a spraying system adapted for use in hand held spraying application.

Reference is now made to FIG. 1 which schematically illustrates a spraying system 10 adapted for use, for example, in a hand held spraying application. The system 10 is configured to separately and/or simultaneously apply an atomized mist of skin treatment liquid and a stream of drying/warming air towards a target surface 12 (for example, a customer's skin). The system 10 comprises a hand held spray member (in this case schematically represented by a dotted enclosing line 101, wherein the enclosing line 101 for the spray member generally indicates the use of any suitable enclosure or housing configuration including, for example, a simple structural mount to which spray member components are mounted or a casing which completely encapsulates the spray member components). The line 101 thus generally represents the support, enclosure or housing configuration of the hand held spray member.

Supported by the support, enclosure or housing configuration 101 of the spray member is a nozzle 104 that includes a spray jet outlet 105. The spray jet outlet 105 of the nozzle 104 sources a finely atomized spray cloud (for example, a mist cloud) 33 of the skin treatment liquid aimed generally in a spray direction 36. Further supported by the support, enclosure or housing configuration 101 is a heated air outlet 108. The heated air outlet 108 sources a relatively lower pressure heated air stream 37 aimed generally in an air direction 38. The spray direction 36 and air direction 38 are both aimed towards the target surface 12. In a preferred embodiment, the spray direction 36 intersects 70 the air direction 38 such that the air stream 37 mixes with the atomized spray cloud 33 prior to atomized spray cloud 33 contact with the target surface 12. Even more particularly, the air direction 38 is aimed such that the air stream 37 mixes with a leading edge 39 of the atomized spray cloud 33 (in terms of a primary direction of hand held spray member movement when applying the skin treatment liquid to the target surface 12).

The nozzle 104 with spray jet outlet 105 may comprise any suitable finely atomizing spray nozzle assembly known to those skilled in the art. For example, the nozzle 104 may comprise any known air-assisted type atomizing nozzle (such as an air atomizing nozzle, a high volume, low pressure (HVLP) nozzle, and the like). In the case of an air-atomizing nozzle, either a single air source or separate air sources may be used for providing relatively lower pressure air for the air stream delivered at the heated air outlet 108 and relatively higher pressure air used by the nozzle 104 to atomize the spray liquid and form the spray cloud 33 (as well as relatively higher pressure air used by the nozzle 104 to shape the pattern of the emitted spray cloud). Alternatively, the nozzle 104 may comprise a suitable hydraulic nozzle, or other type of nozzle such as a sonic nozzle, in which case only a single air source is needed for providing the relatively lower pressure air for the air stream delivered at the heated air outlet 108 (and perhaps also provide the relatively higher pressure air used by the nozzle 104 to shape the pattern of the emitted spray cloud). The nozzle 104 may also support electrostatic spraying of the skin treatment liquid and the system 10 may support ionized application of the heated air stream 37, as discussed in more detail herein.

Also supported by the support, enclosure or housing configuration 101 of the hand held spray member is a liquid control valve 52 coupled between a liquid inlet 53 and the nozzle 104 by ducting. The liquid control valve 52 at the very least controls the state (on/off) of passage of skin treatment liquid received at the liquid inlet 53 to the spray jet outlet 105 of the nozzle 104. In addition, the liquid control valve 52 may further control a rate of flow of skin treatment liquid received at the liquid inlet 53 to the spray jet outlet 105 of the nozzle 104. In either case, the passed skin treatment liquid is atomized at the spray jet outlet 105 to form the spray cloud 33. With respect to controlling the state and rate of flow of skin treatment liquid, the liquid valve 52 may comprise any suitably controlled fluid flow valve (for example, separate from the nozzle 104), and in a preferred implementation, as discussed in more detail herein, may comprise a needle valve adjustment mechanism within the nozzle 104 that acts on the nozzle jet outlet 105. Actuation of the liquid control valve 52 in the hand held spray member implementation is controlled in response to a controller 24 (for example of the trigger-control type 102 which acts to adjust valve 52 position for state control and perhaps rate control).

The liquid inlet 53 is coupled to a liquid source 110. The liquid source 110 is preferably a container that is filled with the skin treatment liquid. That container is preferably an integral component of, or is removably mounted to, the support, enclosure or housing configuration 101 of the hand held spray member (thus obviating the need to tether an external tank to the hand held sprayer). The container is preferably sized to store a relatively small amount of skin treatment liquid (for example, one or a few doses selected for each spray session or application). The container is received by a receptacle 65 formed in the support, enclosure or housing configuration 101 of the hand held spray member and coupled to the liquid inlet 53. In an alternative configuration, the container may instead comprise an external tank configuration storing the skin treatment liquid and coupled to the liquid inlet 53 using a hose.

The reference to a liquid source 110 includes the use of a single liquid tank supplying a single type (or container) of liquid for spray application as well as the use of multiple liquid tanks (or containers) each containing a distinct liquid for customer selection and skin application. When multiple tanks are provided, the customer can design a multi-product spray session. The operation of the system 10 can be adapted to optimize the spray experience based on the liquid selections made by the customer. Selection may be made by the user between the different spray liquid products.

Further supported by the support, enclosure or housing configuration 101 of the hand held spray member is an air heating system 117 coupled to supply heated air to the air outlet 108 that sources the heated air stream 37. The air heating system 117 receives air from an air inlet 114 and heats the air to a higher temperature than the temperature of the air as received. Any suitable heating element could be used within the air heating system 117, that heating element receiving power from a power supply that is either external or internal of hand held spray member. The heating element for the air heating system 117 can be incorporated directly into the air ducting 51 or positioned at the exit of the air outlet 108. In a preferred implementation, as discussed in more detail herein, the heating element for the air heating system 117 is positioned in a handle of the hand held spray member.

The air inlet 114 preferably receives ambient temperature air from an air source (not shown) external to the enclosure or housing configuration 101 of the hand held spray member. The air heating system 117 then heats the received ambient temperature air so that the air stream 37 sourced by the air outlet 108 is warmer than the ambient air temperature (i.e., warmer than the air temperature where the target 12 is located). The heated air output from the air outlet 108 in the heated air stream 37 mixes with the atomized spray cloud 33 prior to spray cloud 33 contact with the target surface 12.

In an alternative implementation, the air heating system 117 (and its air source) is positioned external to the enclosure or housing configuration 101 of the hand held spray member. In this case no internal heating system is needed within the support, enclosure or housing configuration 101 of the hand held spray member, and the air inlet 114 could be directly coupled to the ducting 51 for the air outlet 108.

Actuation of the air heating system 117 in the hand held spray member implementation may be controlled in response to the controller 24, or may be automatically actuated whenever the system 10 is in operation. For example, with respect to an electrically powered air heating system 117, the controller 24 may respond to actuation of the trigger 102 by supplying power to the air heating system 117. As will be discussed in more detail below, with this implementation where actuation of the air heating system 117 generally coincides with actuation of the spraying function, it is important that the air heating system 117 reach a desired heated air temperature as quickly as possible, and further that the air heating system 117 be capable of maintaining that heated air temperature for the duration of the spraying session.

Further supported by the support, enclosure or housing configuration 101 of the hand held spray member is an air valve 121 coupled in the ducting 51 between the air heating system 117 and the air outlet 108. The air valve 121 at the very least controls the state (on/off) of passage of heated air received from the air heating system 117 to the heated air outlet 108. In addition, the air valve 121 may further control a rate of flow of heated air received from the air heating system 117 to the heated air outlet 108. In either case, the passed heated air is delivered from the heated air outlet as the heated air stream 37. With respect to controlling the state and rate of flow of heated air, the air valve 121 may comprise any suitably configured controlled air flow valve, and in a preferred implementation, as discussed in more detail herein, may comprise a flap valve adjustment mechanism. Actuation of the air valve 121 in the hand held spray member implementation is controlled in response to a controller 24 (for example of the trigger-control type 102 which also acts to adjust liquid control valve 52). The control exercised with respect to the air processed by the air heating system 117 and the air valve 121 may comprise one or both of controlling air temperature and/or controlling air flow rate, and this control may be provided through the same controller 24 that controls liquid valve 52 or through a separate controller, as desired. In a preferred implementation, as will be discussed in more detail below, control over the liquid control valve 52 is coordinated with control over the air valve 121. For example, a coordinated inversely proportional control may be implemented where liquid control valve 52 opens as the air valve 121 closes, and vice versa. Alternatively, a coordinated alternate control may be implemented where liquid control valve 52 is open (or partially open) while air valve 121 is closed (or partially closed), and vice versa. Still further, a coordinated control may be implemented where multiple modes are supported with respect to opening and closing of the valves 52 and 121. Additionally, the controller 24 can also switch on and off of the heating system 117.

The source of air supplied to inlet 117 is preferably an ambient air supply using, for example, a fan, blower or compressor. The compressor of the air supply may be any suitable air moving device, such as a fan, blower, turbine, or piston, rotary or diaphragm compressor, or other air pump. The operation of the air supply may itself provide sufficient heating of the air, thus obviating the need for an additional heating element to heat the air within the hand held spray member. For example, when a high volume, low pressure (HVLP) nozzle (see, FIG. 2) is used for nozzle 104, the nozzle's air turbine itself, when in operation, will act as a heated air source. Additionally, if an air atomizer is used for the nozzle 104 it is preferred to use a common compressor (air supply) for sourcing higher pressure air for both air atomization at the spray jet outlet 105 (and perhaps pattern shaping of the spray cloud) and the supply of lower pressure heated air at the air output 108, rather than have a separate source of air for each.

The controller 24 for the hand held spray member is used not only to control delivery production of the spray cloud 33, but is further used to control delivery of the air stream 37. This control can be exercised through actuation of a triggering mechanism 102 at the controller 24. In particular, through the use of the trigger controller 102, the user may control the delivery of liquid spray from the nozzle spray jet outlet 105 and/or the delivery of heated air from the air outlet 108 (and perhaps other air outlets, as well) before, during or after the liquid spray is applied. In essence, the controller functions to control the application of the liquid spray and heated air (for example, simultaneously or sequentially/alternatively).

The controller 24 may comprise any suitable electrical, mechanical, or electro-mechanical control system that is responsive to user actuation to control operation of the hand held spray member in support of the various operating modes described herein. For example, the controller 24 may control actuation of the liquid control valve 52 in connection with controlling the supply of liquid, and also control actuation of the air valve 121 in connection with controlling the delivery of heated air in the air stream 37. The controller 24 may additionally control a proportional division of heated air for output in the lower pressure air stream and for use as higher pressure atomization and pattern shaping air at the nozzle 104. In addition, the heated air may be delivered through any included the atomizing port(s) and pattern shaping port(s). The controller 24 may further control operation of the heating system 117 so as to control the temperature of the heated air in the air stream 37.

The system implements a number of safety features. First, the air heating system 117 includes a thermal switch and a thermal fuse to detect malfunction, improper operation or dangerous conditions in the air heating system 117 itself. These features may operate to self-control the air heating system 117 and may further be used as sensors to provide output information used by the controller 24 with respect to safely controlling system operation. The controller 24 may sense operating conditions of the system, for example, temperature, air flow, liquid flow, electrical problems (shorts, opens, over-current, over-voltage, power, ground faults, error messages, and the like), and respond to control operation of the system. For example, the controller may sense an over temperature condition within the air heating system 117 and cut off power supplied to the air heating system 117. As another example, the controller may sense reduced or absent air flow at the air inlet and cut power from the air heating system 117 to prevent overheating. The controller may further sense reduced or absent liquid flow and provide a warning signal or otherwise change operating mode of the system. The controller could still further monitor the operation of any equipment, such as an air supply or power supply, coupled to the hand held sprayer and respond to errors or problems in that equipment with a change of operation for the sprayer. The equipment coupled to the sprayer may also detect disconnection of the sprayer and terminate supply of air and power. Lastly, the controller supports implementation of a cool-down mode at the end of a spraying session to pass air through the heating system.

In a preferred embodiment, the production of the spray cloud 33 output from spray jet outlet 105 of the nozzle 104 is controlled separately from the delivery of heated air in the air stream 37 output from air outlet 108 to allow a sequence of operations to be performed in connection with the spraying skin treatment, such as pre-warming of the skin (without spraying), followed by separate spraying (with warming air) and drying (without spraying) cycles. The air stream 37 output from the air outlet 108 is provided in a controlled manner for a number of purposes: to pre-warm the skin, to warm the edge of the spray cloud 33 as the atomized spray jet is naturally bent due to movement of the hand held spray member, and to provide a drying air stream after a spray operation.

The ability of the system to move among and between various operating modes is designed to enhance the consumer's spray tanning experience and improve the tanning result. Warm air from the air drying outlet serves to prepare the skin for treatment, warm the skin for customer comfort, and dry the skin evenly after application. Alternating between spray application and warm air application improves the tanning result. Furthermore, mixing warm air application with the spray cloud 33 reduces the discomfort experienced by the consumer due to temperature drop of the spray liquid.

Reference is now made to FIG. 2 which illustrates an exemplary implementation of a hand held sprayer of the type shown in FIG. 1. The support, enclosure or housing configuration 101 of the hand held spray member implementation includes a suitably sized and shaped housing (or shroud) 112 for containing the nozzle 104, air outlet 108, ducting for air and liquid flow, valves 52 and 121 for controlling liquid and air flow, air heating system 117 and the trigger-type 102 control 24 functionality for controlling operation of the hand held spray member. In an exemplary configuration, the housing 112 includes a barrel shaped portion 94 and a handle shaped portion 96.

The front of the enclosure or housing configuration 101 of the hand held spray member implementation shows use of a spray nozzle 104 of the air atomizing type with the spray jet outlet 105 and first air ports 106 provided immediately adjacent the nozzle spray jet outlet 105 and a second air port 91 provided annularly surrounding the spray jet outlet 105. The first air ports 106 supply relatively higher pressure air used by the nozzle 104 for pattern shaping of the spray cloud, for example, to shape the spray cloud into a flat fan-like spray shape. The second air port 91 supplies relatively higher pressure air used by the nozzle for atomization of the spray liquid to create the spray cloud. The front of the support, enclosure or housing configuration 101 of the hand held spray member implementation further shows the air outlet 108 for supplying relatively lower pressure air for mixing with the spray cloud separate and apart from the nozzle 104 and its air ports 91 and 106. It will be understood that the relatively lower pressure air supplied from the air outlet 108 is output in a separate and distinct air stream 37 from the relatively higher pressure air supplied to the air ports 105 and 91 which is output for atomization and pattern shaping. Thus, in this particular implementation, the air supplied from the air outlet 108 may be referred to as "supplemental" air, meaning that this air supplied supplemental to the atomization and pattern shaping air supplied from the air ports 91 and 105. Furthermore, it should be understood that the pattern shaping air port 105 could provide the functionality of the air outlet 108 to supply warming air to the spray cloud (and thus obviate the need for the air outlet 108) provided that the air output from the pattern shaping air port 105 could be satisfactorily supplied for pattern shaping at a relatively lower pressure which would not contribute to the cooling effect of nozzle expansion.

Figure 2:
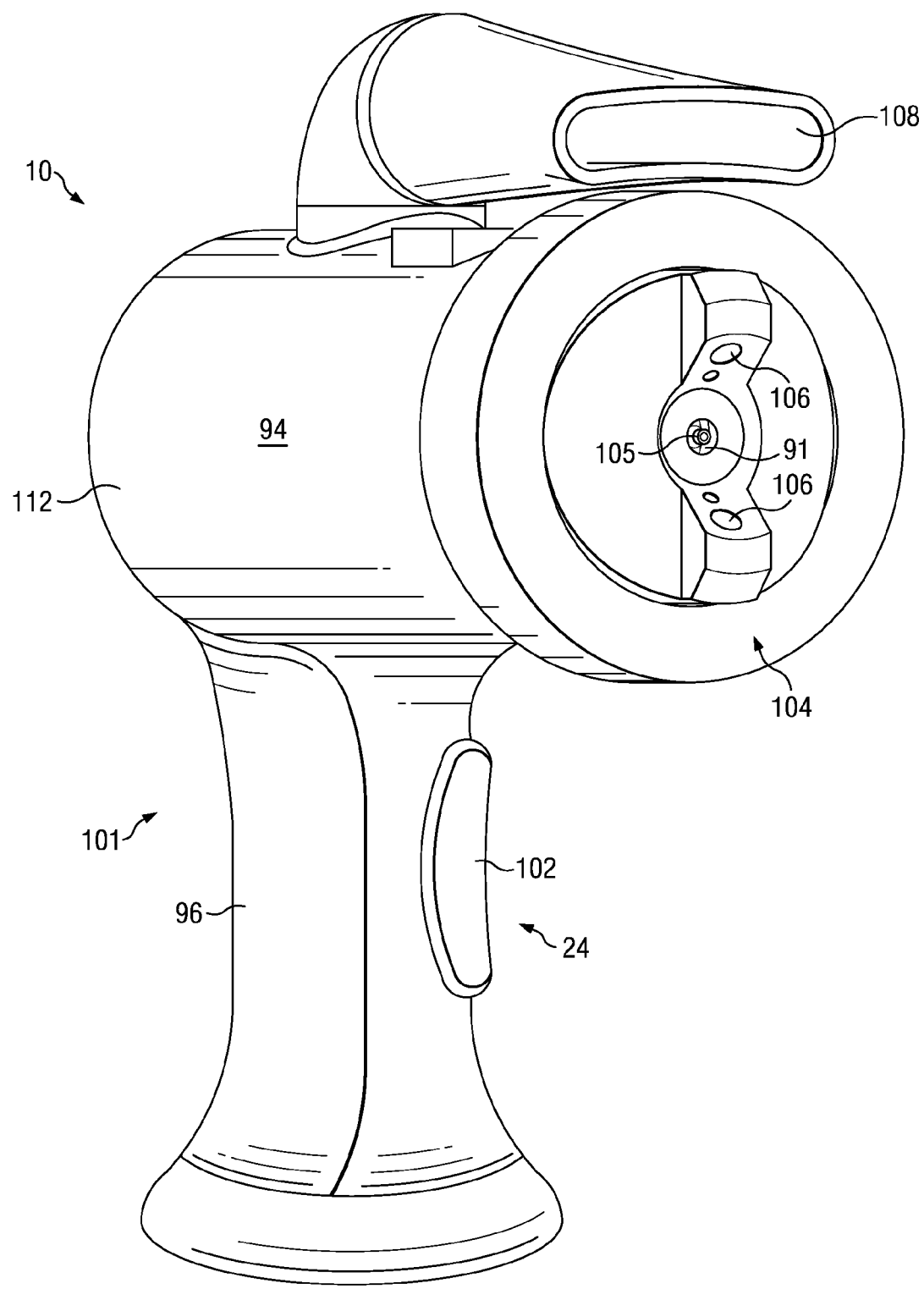
FIG. 2 illustrates an exemplary implementation of a hand held sprayer of the type shown in FIG. 1.

The physical embodiment of the housing 112 illustrated in FIG. 2 for the enclosure or housing configuration 101 of the hand held spray member implementation is exemplary in nature, it being understood that any suitable industrial design for the housing could be used. What is critical is that the design is capable of being hand held and further support a suitably positioned trigger-type 102 control 24 functionality on the outside surface of the housing. The illustration in FIG. 2 of a traditional gun-shaped housing design with a barrel and handle for the hand held spray member is not to be considered as critical or limiting.

Although FIGS. 1 and 2 illustrate the use of only a single air outlet 108, it will be understood that two (or more) air outlets could instead be provided (for example, one above and one below nozzle spray jet outlet 105). What is desired in a moving nozzle 104 implementation, like that provided with a hand held spray member implementation, is that an air outlet 108 providing heated air in an air stream 37 be located on at least the leading edge of the predominant direction of nozzle motion during spraying (for example, with an upward motion in the case of the illustrated hand held spray member and nozzle). The air outlet 108 is configured to deliver the heated air stream 37 into the spray cloud 33, and it is an advantage of the disclosed system that this heated air is delivered towards the customer and is felt on the customer's skin when or before the spray cloud 33 impacts the customer's skin. In the case of an embodiment with two air outlets 108, these outlets are preferably positioned so as to direct an air stream 37 on both the leading edge 39 and trailing edge 41 (see, FIG. 1) of the spray cloud 33 with respect to the predominant direction (for example, vertical) of hand held spray member movement so as to allow for an optimal mixing of warm air with the spray cloud (on the leading edge) and provide a drying effect after the spray passes over the skin (on the trailing edge).

Figure 3:
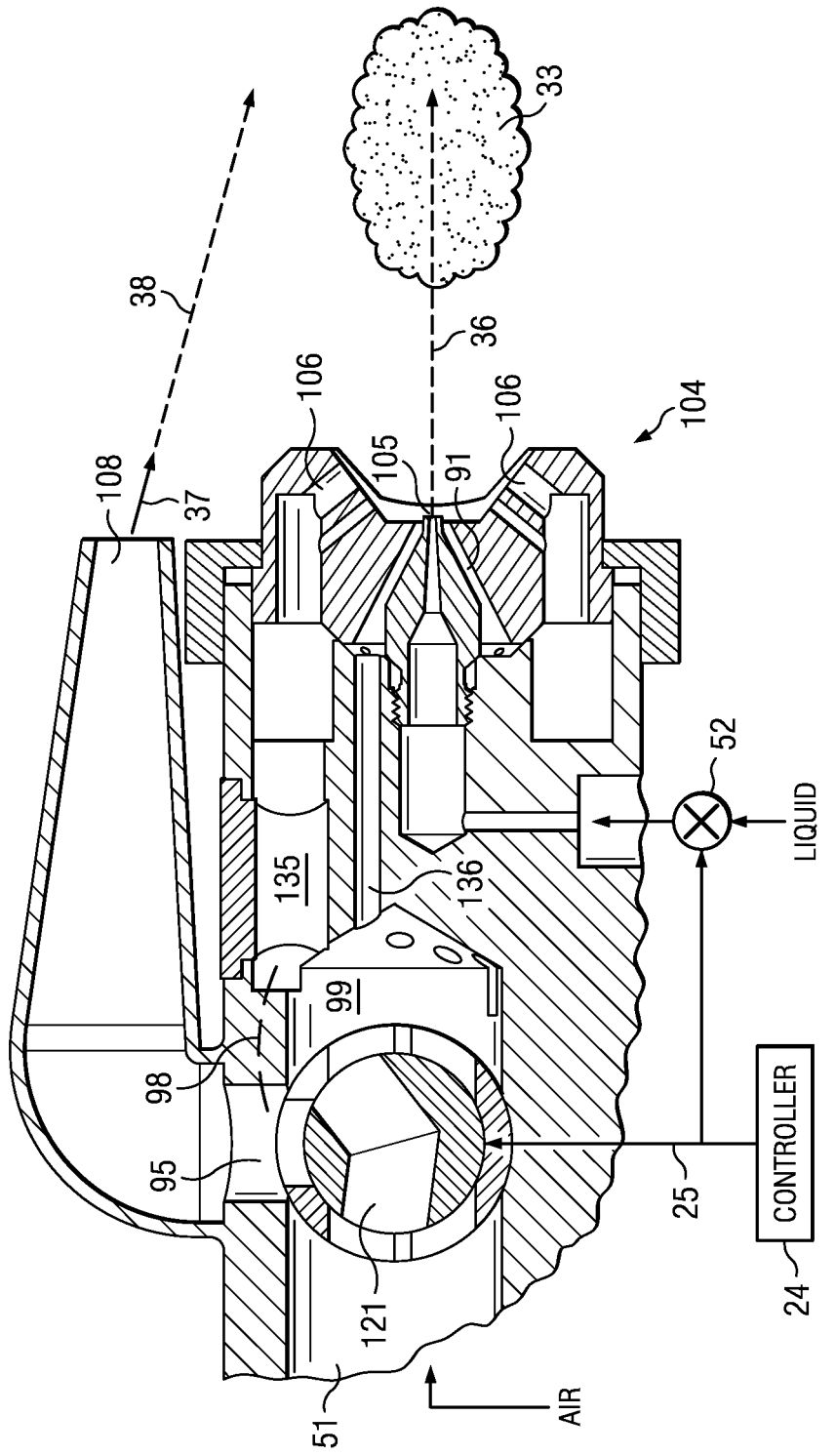
FIG. 3 illustrates a cross sectional view of a portion of the hand held sprayer shown in FIG. 2 focusing on the nozzle.

Reference is now made to FIG. 3 which illustrates a cross sectional view of a portion of the hand held spray member shown in FIG. 2. The nozzle 104 used in this implementation is of an HVLP type, but could comprise any air-assisted atomizing nozzle needing an air flow for creating the spray cloud. The air valve 121 is implemented as a spool valve which operates responsive to controller 24 to control the flow of received heated air to (and among and between) the higher pressure pattern shaping air port 106, the higher pressure atomizing air port 91 and the lower pressure "supplemental" air outlet 108 on the front of the nozzle. Liquid for spraying is passed from liquid valve 52 by internal ducting to the nozzle spray jet outlet 105 where it is atomized in response to the air supplied at the air port 91 to form the atomized spray cloud and pattern shaped in response to the air supplied at the air ports 106 so as to shape the atomized spray cloud (for example, into a fan-like pattern). Heated air is passed by internal ducting and distributed among and between the air ports 91 and 106 and the air outlet 108. The amount of heated air delivered to the air ports 91 and 106 and the air outlet 108 is proportionally adjusted by actuation of the spool-type air valve 121. The proportional adjustment is preferably made under the control of the user. In a preferred implementation, the proportional adjustment is effected by the user through the trigger-type controller (reference 24, FIG. 1) which actuates, through an appropriate electrical, mechanical or electro-mechanical system 25, a coordinated operation of both the liquid valve 52 and air valve 121.

In an alternative configuration, the air ports 106 may be configured to not only shape the atomized spray cloud but also to provide heated air for purposes of warming the spray cloud. In this implementation, the "supplemental" air outlet 108 could be eliminated. To implement this configuration, however, the internal ducting of the nozzle 104 is configured so that the pattern shaping air ports 106 receive the heated air. Additionally, the pattern shaping air ports 106 must be designed to be low pressure outlets that do not induce a nozzle cooling effect on the spray cloud. In instances where higher pressure ports are needed to produce the desired pattern shaping and spreading of the spray cloud, it will be necessary to further include the "supplemental" air outlet 108 as a low pressure port supplying heated air for the purpose of warming the spray cloud.

While FIG. 3 shows that the atomizing air port 91 also receives heated air, it will be understood that the ducting of the nozzle 104 may be configured to instead supply ambient air to the atomizing air port 91 while the air heating system (reference 117, FIG. 1) is provided within the ducting leading to the pattern shaping air ports 106.

Although FIG. 3 illustrates that the air channel 135 coupled to the pattern shaping outlets 106 and the air channel 136 coupled to the air atomization outlet 91 are connected to receive a common supply of air at area 99, it will be understood that the air channel coupled to the pattern shaping outlets 106 could instead be connected receive the same supply of air as the air outlet 108 at area 95. This could be accomplished by forming a ducting connection as shown by the dotted line 98 between area 95 and the air channel 135 (and severing the connection between area 99 and the air channel 135).

Figure 4A:
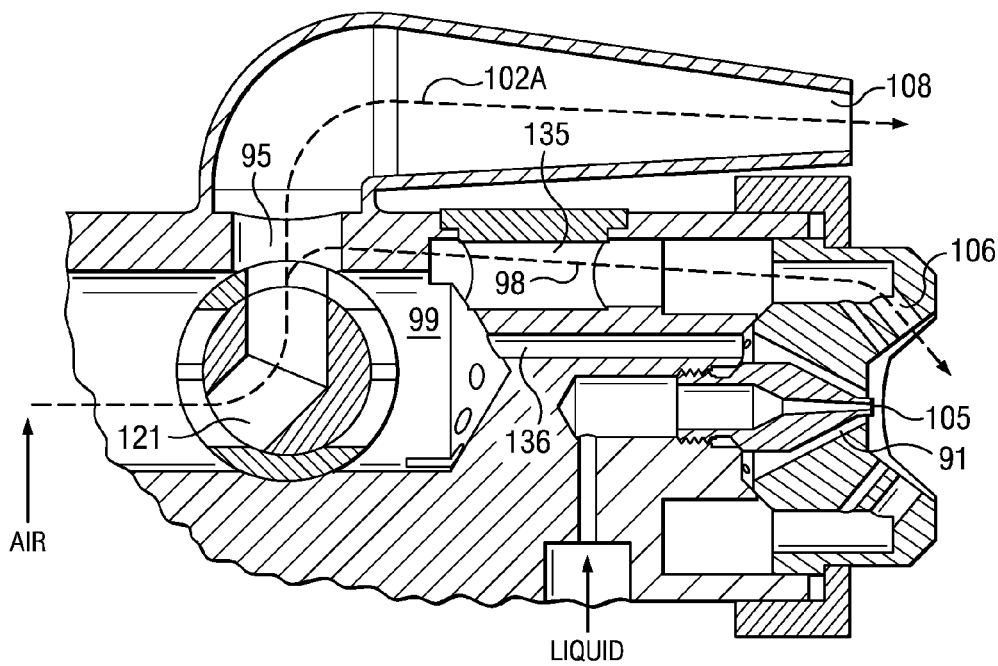
FIGS. 4A to 4C illustrate modes of operation for the nozzle portion shown in FIG. 3.
Figure 4B:
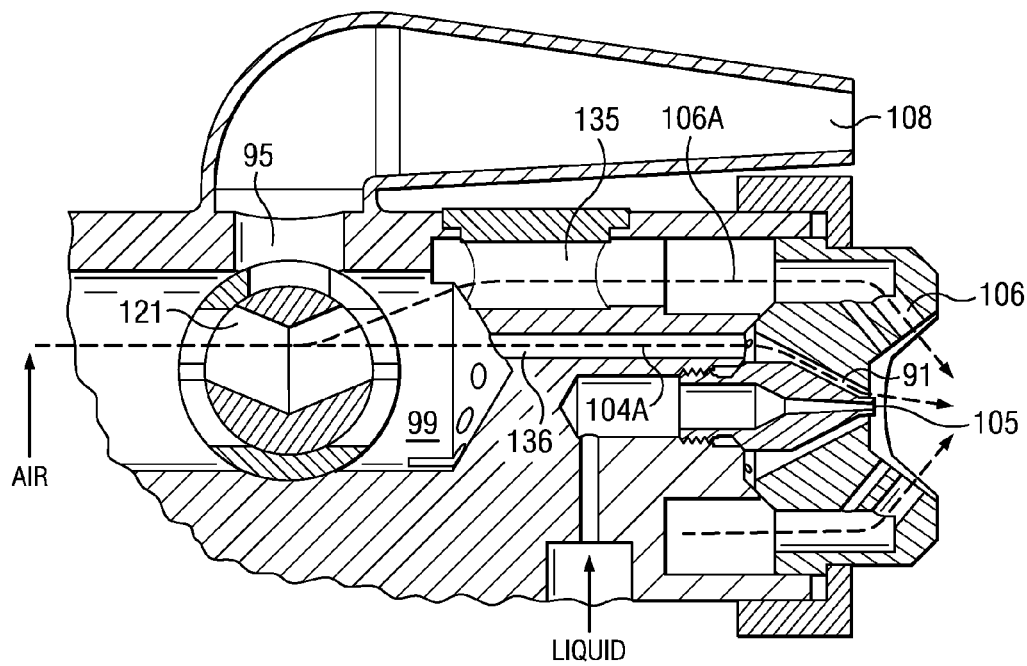
Figure 4C:
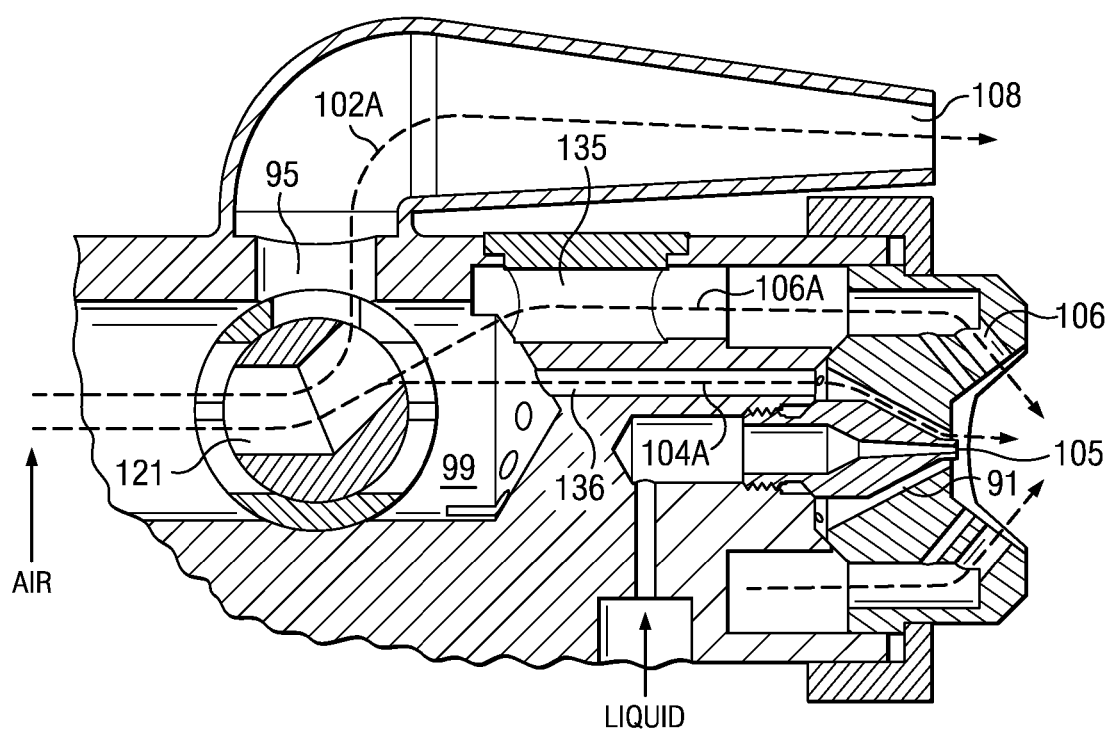

FIGS. 4A, 4B and 4C show that by rotating the spool-type air valve 121 heated air can be proportionally directed between the air outlet 108 and the air outlets 106 and 91 for spray atomization and pattern shaping. In this way the nozzle 104 can be controlled into multiple modes of operation.

In a first mode, as shown in FIG. 4A, the air valve 121 is controlled to be in a position for directing received heated air to the lower pressure "supplemental" air outlet 108 (but not the higher pressure atomizing and pattern shaping ports 91 and 106) via the area 95 and along path 102A. In the first mode, the controller may additionally turn off the liquid valve (reference 52, FIG. 1) supplying spray liquid to the nozzle spray jet outlet 105. It will be recognized that in this first mode, with the alternative configuration including the dotted line 98 connection from area 95 to air channel 135 (as shown in FIG. 3), the received heated air would be directed by the valve 121 to both the "supplemental" air outlet 108 and to the pattern shaping ports 106 (but not the atomizing port 91).

In a second mode, as shown in FIG. 4B, the air valve 121 is controlled to be in a position for directing air to the higher pressure atomizing and pattern shaping ports 91 and 106 (but not the lower pressure "supplemental" air outlet 108) via area 99 and along paths 104A and 106A. In the second mode, the controller may additionally turn on the liquid valve (reference 52, FIG. 1) supplying spray liquid to the nozzle spray jet outlet 105. It will be recognized that in this second mode, with the alternative configuration including the dotted line 98 connection from area 95 to air channel 135 (as shown in FIG. 3), received heated air would be directed by the valve 121 to the air atomizing port 91 (but not the "supplemental" air outlet 108 and pattern shaping ports 106).

In a third mode, as shown in FIG. 4C, the air valve 121 is controlled to be in a position for directing air (in a selected proportion) to both the higher pressure atomizing and pattern shaping ports 91 and 106 and the lower pressure "supplemental" air outlet 108 along paths 102A, 104A and 106A in a proportional manner. The atomizing and pattern shaping ports 91 and 106 receive air from area 99 while the "supplemental" air outlet 108 receives air from area 95, the amount of air in each area being proportionally controlled by the position of the valve 121. In this third mode, because the supplied air is being proportionally shared between the atomizing and pattern shaping ports 91 and 106 and the "supplemental" air outlet 108, it may be necessary for the controller to additionally control the liquid flow valve (reference 52, FIG. 1) and the amount liquid being delivered to the nozzle spray jet outlet 105. Alternatively, if a pressurized liquid reservoir (tank) is used, the user may instead selectively perform a venting action to reduce liquid pressure within the tank in proportion to the reduction of air being supplied to the atomizing and pattern shaping ports 91 and 106. It will be recognized that in this third mode, with the alternative configuration including the dotted line 98 connection from area 95 to air channel 135 (as shown in FIG. 3), a different proportional relationship with respect to the delivery of heated air to the pattern shaping ports 106 is provided because the pattern shaping ports 106 will receive air from area 95 instead of area 99.

Figure 5:
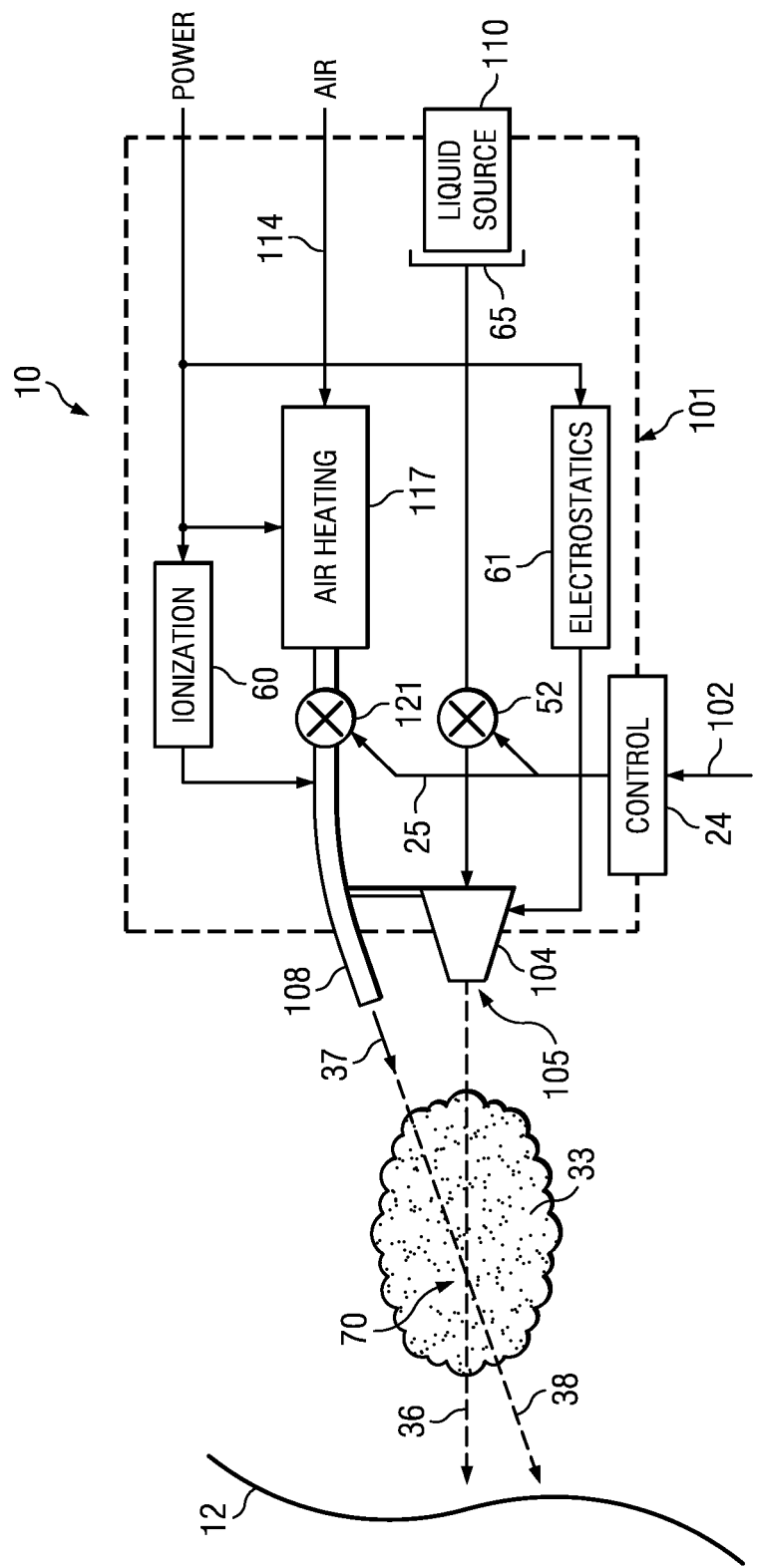
FIG. 5 schematically illustrates an alternative implementation of a spraying system adapted for use in a hand held spraying application.

Reference is now made to FIG. 5 which schematically illustrates an alternative implementation of a spraying system 10 adapted for use, for example, in a hand held spraying application. The use in FIG. 5 of structures and reference numbers identical to those shown in FIG. 1 indicates the use in FIG. 5 of same or similar components. Further description of those same or similar components will not be provided in connection with the description of FIG. 5 unless necessary to explain additional components and features.

Further supported by the support, enclosure or housing configuration 101 is an air ionization system 60 coupled to the ducting which delivers heated air to the air outlet 108. The air ionization system 60 functions to ionize the heated air which forms the air stream 37. The air ionization system 60 may receive power from the same external power supply which supplies power to the heating system 117. The ionization of the air delivered from the air outlets of the system will assist in charging the spray cloud so as to improve coating uniformity and reduce overspray.

Further supported by the support, enclosure or housing configuration 101 is an electrostatics system 61 coupled to the nozzle 104 which, in a preferred implementation, inductively charges the spray cloud 33 output from the nozzle jet 105. The electrostatics system 61 may receive power from the same external power supply which supplies power to the heating system 117. It will be understood, however, that other forms of electrostatic charging may be implemented, including contact charging in which the electrostatic charge is applied to the liquid which is received by the hand held spray member. Electrostatically charging the spray cloud will improve coating uniformity and reduce overspray.

Reference is now made to FIG. 6 which illustrates an exemplary implementation of a hand held sprayer of the type shown in FIG. 1 and having a similar configuration to that shown in FIG. 2. This external view shows the housing (or shroud) 112, the nozzle 104, nozzle jet outlet 105, pattern shaping air ports 106 and heated air outlet 108. The liquid source 110 is attachable to a rear of the barrel portion 94 of the sprayer. The liquid source 110 comprises a single liquid tank supplying a single type of liquid for spray application. The tank may be filled through a cap 111. The container forming the liquid source 110 is also detachable through actuation of a mechanical release button 113. This allows the user to change the type of spray liquid being applied by changing liquid containers. The air inlet 114 is provided at a base of the handle portion 96. Tubular member 115 supports connection of an air hose to the hand held sprayer. The controller 24 of the sprayer includes an external trigger 102. The limit of trigger 102 actuation is controlled by a set screw 103.

Reference is now made to FIG. 7 which illustrates a cross sectional view of the hand held sprayer shown in FIG. 6. Air is received at the air inlet 114 at the base of the handle portion 96. The received air passes up through the handle portion 96. The air heating system 117 is installed in the handle portion 96 within the ducting carrying the air received at inlet 114.

The heating system 117 includes a thermal fuse 118 and a thermal switch 119 (in the form, for example, of a thermostat) functioning as safety devices with respect to sprayer operation so as to protect against an overheating or malfunctioning situation. A perspective, partially broken away view of the heating system 117 is shown in FIG. 8A. A longitudinal cross-section is shown in FIG. 8B. A lateral cross-section is shown in FIG. 8C. Power to the heating system 117 is supplied by power lines 200. The heating system 117 includes a cylindrical tube support 202. A ceramic core 204 is installed within the tube support 202. A mica wrap 206 is positioned between the inner surface of the tube support 202 and the outer periphery of the ceramic core 204. The ceramic core 204 is formed to include a central longitudinal channel 208 and a plurality of peripheral longitudinal channels 210. These channels 208 and 210 are sized to permit the flow of air through the heating system 117. The power lines 200 pass through the central longitudinal channel 208, and the thermal fuse 118 and thermal switch 119 are installed within the central longitudinal channel 208. A coiled resistance wire 212 is installed within each one of the peripheral longitudinal channels 210. The coiled resistance wires 212 are electrically connected to each other and to the power lines 200.

The heating system 117 is designed to quickly ramp up to a desired air heating temperature and maintain that temperature over the course of a spray session. FIG. 8D is a graph showing air temperature at the output of the heating system 117 for three different power configurations (low, medium and high). The graph shows how temperature quickly rises from an ambient (or near ambient) air temperature to an elevated temperature level. In a preferred operational scenario, the heating system 117 is controlled on initial start up of the spray system in the high power configuration so as to achieve fast temperature rise time. The system may then switch operational power to a reduced medium or low power level depending on user desire and comfort.

Reference is once again made to FIG. 7. After passing through the heating system 117, the air (now heated air) passes through internal ducting and is made available within the hand held sprayer for a number of purposes. First, the heated air is delivered to a heat port air channel 128. This heat port air channel 128 is coupled to the heated air outlet 108 through the air valve 121 for relatively low pressure air delivery in the air stream 37. The air valve 121 in the illustrated configuration comprises a flap valve. The flap valve is mounted to a pivot point 130 and is actuated by the controller 24 in a manner to be described in response to trigger 102 actuation. When closed, the flap valve stops the flow of heated air from heat port air channel 128 to the heated air outlet 108.

Second, the heated air in the heat port air channel 128 is coupled through an inlet check valve 123 to the liquid supply 110 container. The check valve 123 only permits air to enter the liquid supply 110 container, and thus the air supplied from the heat port air channel 128 functions to pressurize the liquid supply 110 container. Third, the heated air is delivered to a nozzle air channel 129 (separate from the heat port air channel 128). This nozzle air channel 129 is coupled to the pattern shaping air ports 106 (through pattern shaping air channel 135) so as to supply relatively higher pressure pattern shaping air for the nozzle 104. This nozzle air channel 129 is further coupled to the air atomization ports 91 (through atomization air channel 136) so as to supply relatively higher pressure atomizing air at the spray jet outlet 105 of the nozzle 104. It will be understood that the air pressure in the heat port air channel 128 and nozzle air channel 129 is dependent on the actuation of the air valve 121. As the air valve 121 closes, pressure rises in the heat port air channel 128 and nozzle air channel 129 thus providing increased air flow at the pattern shaping air ports 106 and air atomization ports 91. Conversely, as the air valve 121 opens, pressure decreases in the heat port air channel 128 and nozzle air channel 129 due to the delivery of the heated air stream 37 from the low pressure heated air outlet 108 (and thus reduced air flow will be available at the pattern shaping air ports 106 and air atomization ports 91).

The controller 24 for the hand held sprayer includes a trigger 102 mounted to the handle portion 96. A first end of the trigger 102 is mounted to a pivot 147. The other end of the trigger actuates a control linkage mechanism (to be described) of the controller 24 through a pin 220. When the trigger 102 is actuated, the trigger mechanism rotates about the pivot 147 and applies force against the pin 220. Movement of the pin 220 (in response to the force applied by actuation of the trigger 102) causes the control linkage mechanism of the controller 24 to move the air valve 121 (i.e., adjust its open/closed condition). When the trigger 102 is in a fully released position, the control linkage mechanism of the controller 24 permits the air valve 121 to assume a fully open position. As the trigger 102 is actuated, the control linkage mechanism of the controller 24 begins to close the air valve 121. As the trigger 102 moves towards the fully actuated position, the control linkage mechanism of the controller 24 moves the air valve 121 towards a fully closed position. The set screw 103 provides a mechanism for controlling the maximum degree of trigger 102 actuation and thus can limit the degree of closure of the air valve 121 in response to full actuation of the trigger 102.

The liquid for the spraying operation is sourced from the liquid supply 110 container. The liquid in the liquid supply 110 container is coupled through an outlet quick connect valve 122 through internal ducting (not explicitly shown) to the nozzle spray jet outlet 105. The nozzle 104 is of the air-assisted atomizing type. High pressure air exiting from the air atomization port 91 atomizes the liquid provided from the liquid supply 110 container and passing through the quick connect valve 122 and internal ducting to the nozzle spray jet outlet 105 to form the spray cloud 33. The outlet quick connect valve 122 for the liquid supply 110 container in this implementation does not function to control the state or rate of fluid flow or the size of the atomized spray cloud. Rather, a separate liquid control valve 52 is provided in the nozzle 104. This liquid control valve 52 in the illustrated configuration comprises a needle valve (to be described) associated with the nozzle jet outlet 105.

When the liquid control valve 52 is closed, the flow of liquid from the liquid supply 110 container to the nozzle spray jet outlet 105 is blocked. As the liquid control valve 52 opens, liquid from the liquid supply 110 container flows to nozzle spray jet outlet 105. This flow is assisted by the fact that the liquid supply 110 container has been pressurized by heated air passing into the liquid supply 110 container through the inlet check valve 123. In a non-needle valve implementation, the outlet check valve 122 may be configured to implement the functionality of the liquid control valve 52 (for example through controlling suction of liquid from the liquid supply 110 container to nozzle spray jet outlet 105).

As discussed above, the controller 24 for the hand held sprayer in a preferred implementation controls at least the state of, and perhaps also the rate of fluid flow provided by, the liquid control valve 52. In the preferred needle valve configuration, the needle valve comprises a fluid flow needle 131 for the liquid control valve 52 that is biased by a spring 133 in a closed position that shuts off the flow of liquid to the nozzle spray jet outlet 105. The fluid flow needle 131 moves within the nozzle 104 in response to actuation of a pin 132. When the trigger 102 is actuated, the trigger mechanism rotates about the pivot 147 and engages the pin 220. Movement of the pin 220 (in response to the trigger 102 actuation) causes the control linkage mechanism of the controller 24 to move the needle valve pin 132 and open the liquid control valve 52 by moving the fluid flow needle 131 moves within the nozzle 104. When the trigger 102 is in a fully released position, the control linkage mechanism of the controller 24 (along with spring 133) sets the fluid flow needle 131 of liquid control valve 52 into a fully closed. As the trigger 102 is further actuated, the control linkage mechanism of the controller 24 begins to open the needle valve (after a delay as described below). When the trigger 102 moves towards the fully actuated position, the control linkage mechanism of the controller 24 sets the fluid flow needle 131 into a position where the liquid control valve 52 is fully open. The set screw 103 provides a mechanism for controlling the maximum degree of trigger 102 actuation and thus can limit the degree of opening the liquid control valve 52 in response to full actuation of the trigger 102.

Figure 6:
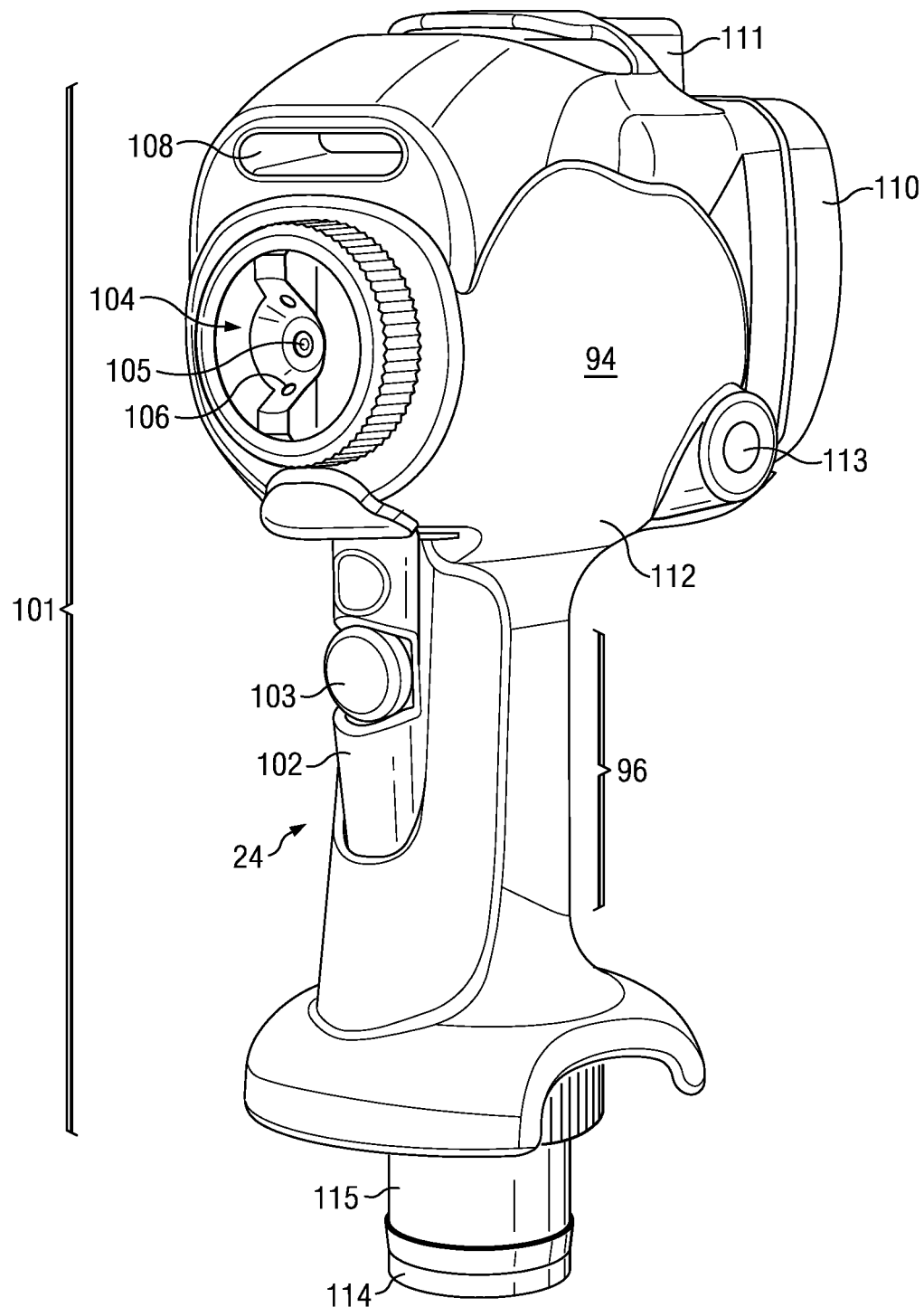
FIG. 6 illustrates an exemplary implementation of a hand held sprayer of the type shown in FIG. 1.
Figure 7:
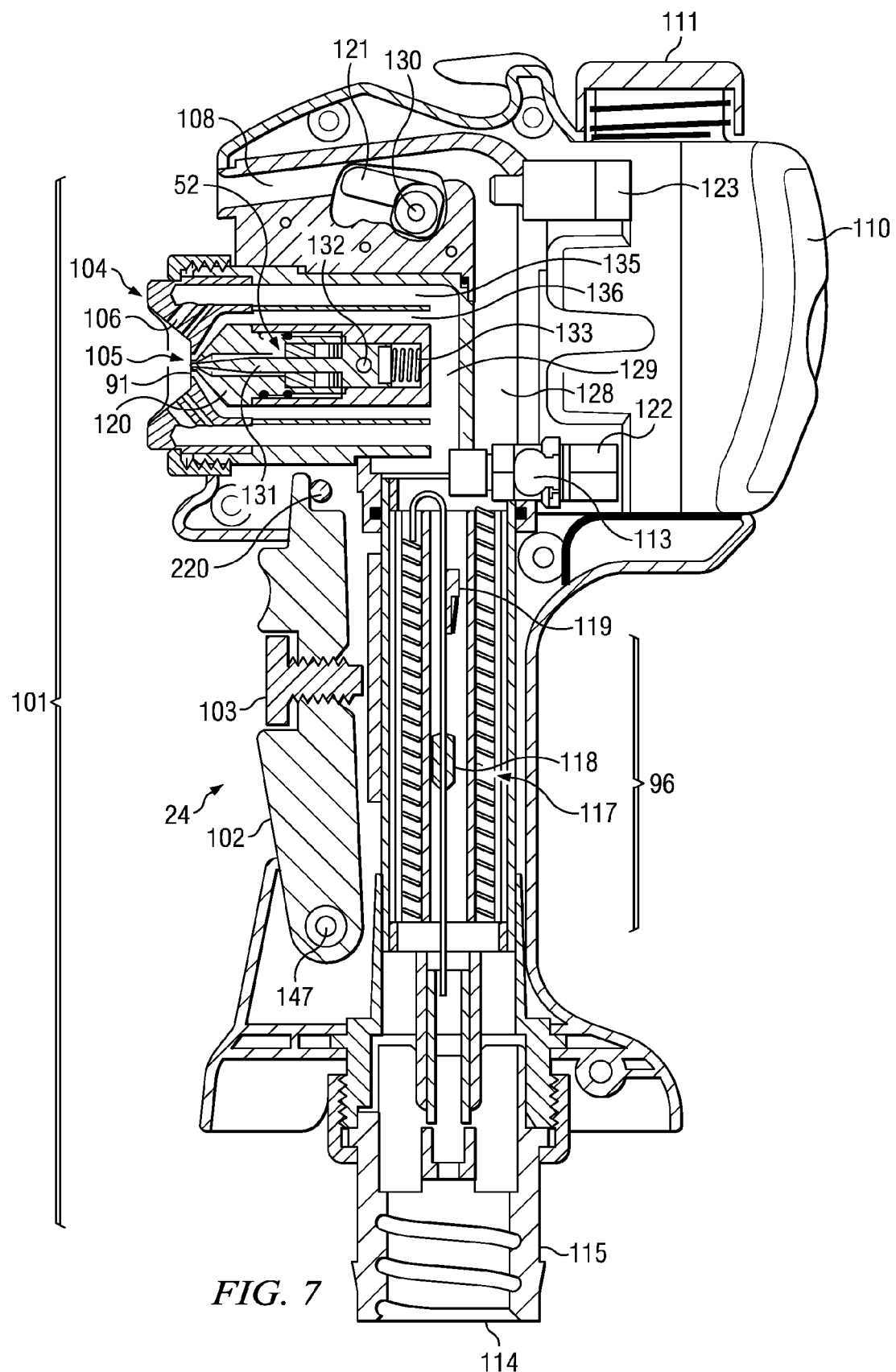
FIG. 7 illustrates a cross sectional view of the hand held sprayer shown in FIG. 6.
Figure 8A:
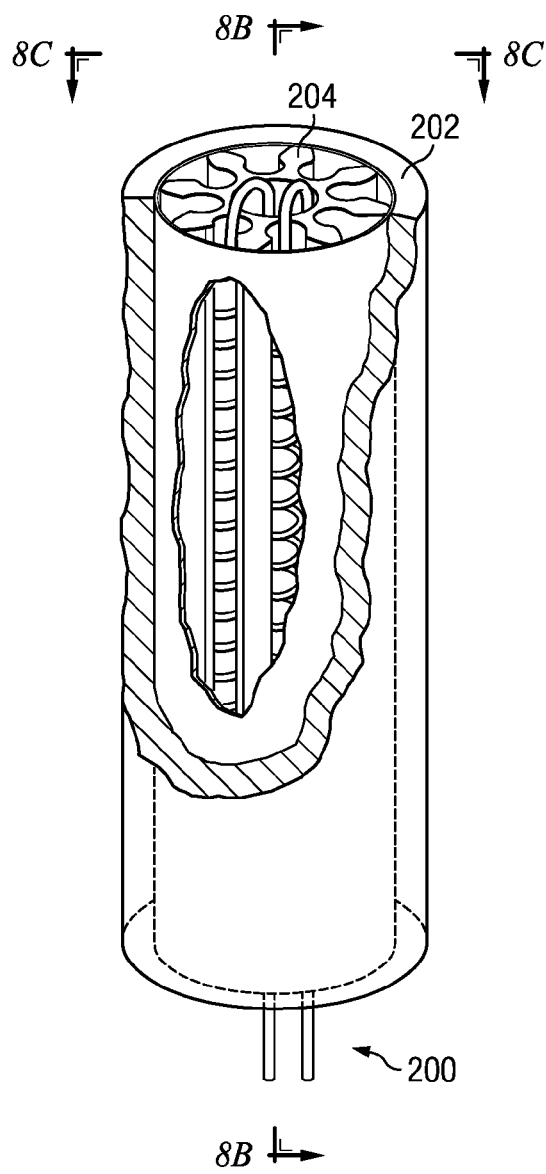
FIGS. 8A to 8C illustrate various views of an air heating system used within the hand held sprayer of FIGS. 6 and 7.
Figure 8B:
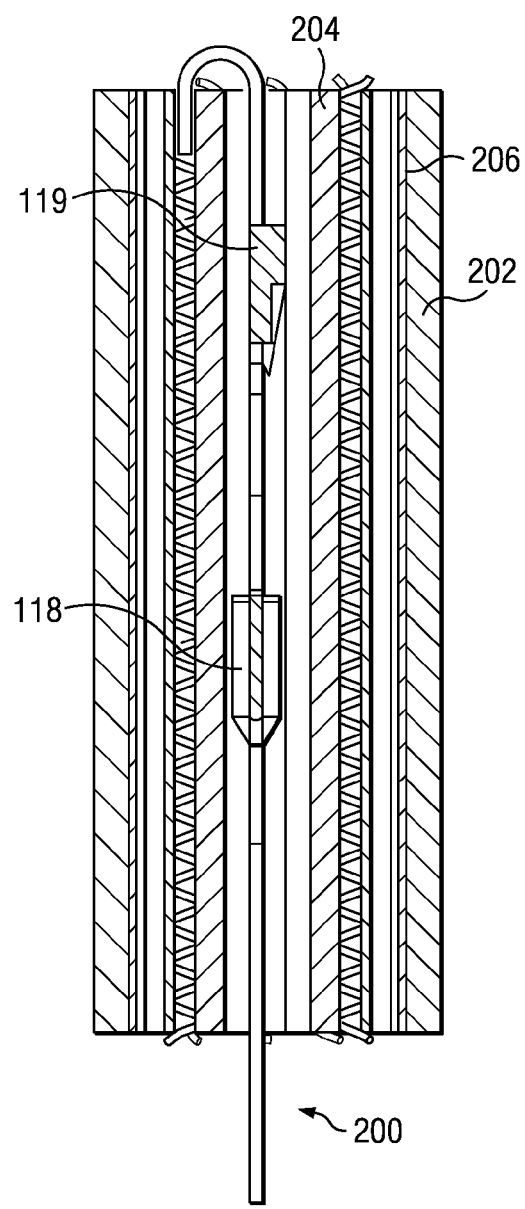
Figure 8C:
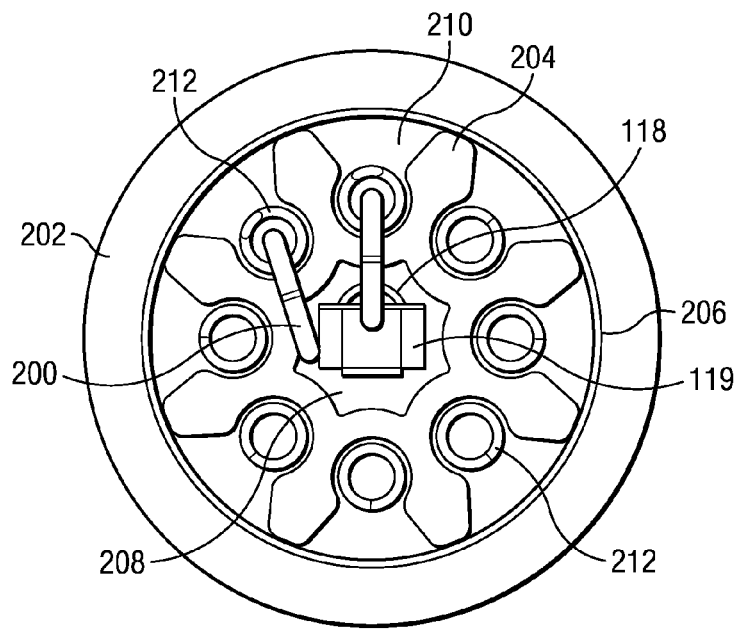
Figure 8D:
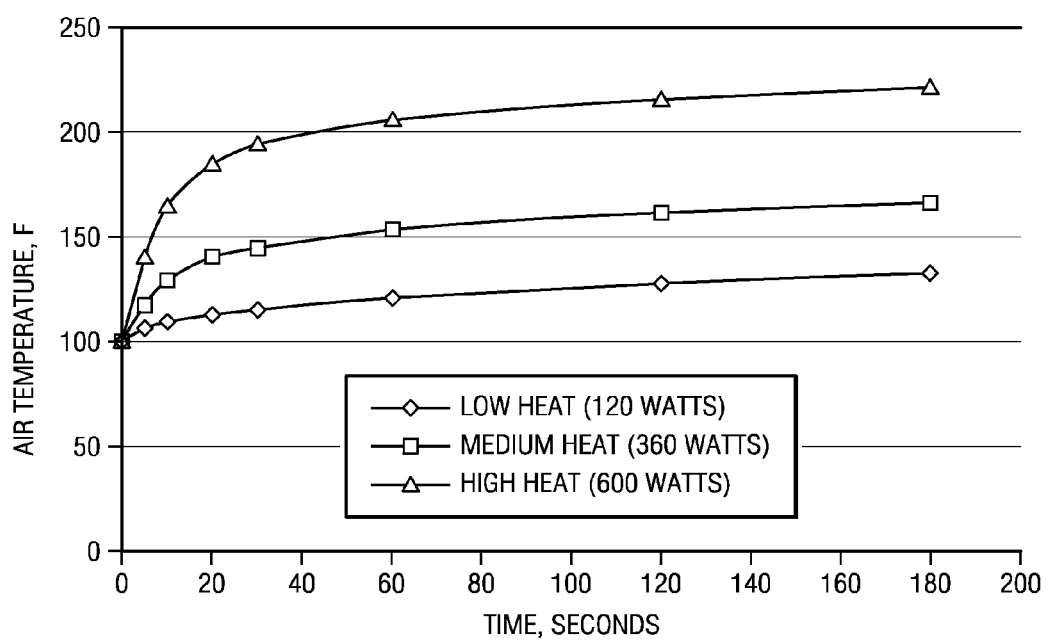
FIG. 8D illustrates a graph of heater operation in multiple modes.
Figure 9A:
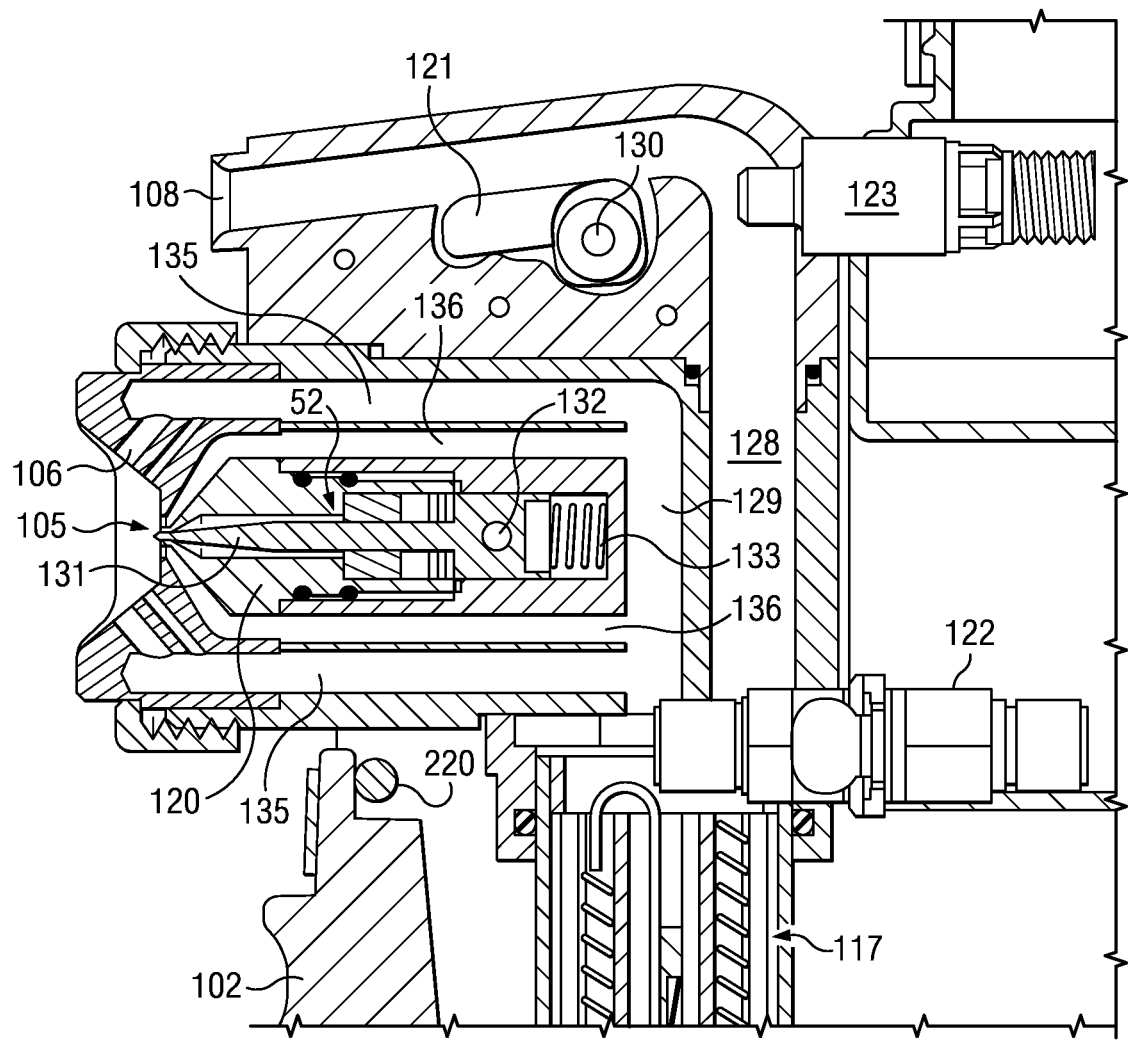
FIGS. 9A to 9C illustrate cross sectional views of the hand held sprayer shown in FIG. 6 focusing on the operation of the air and liquid control valves.
Figure 9B:
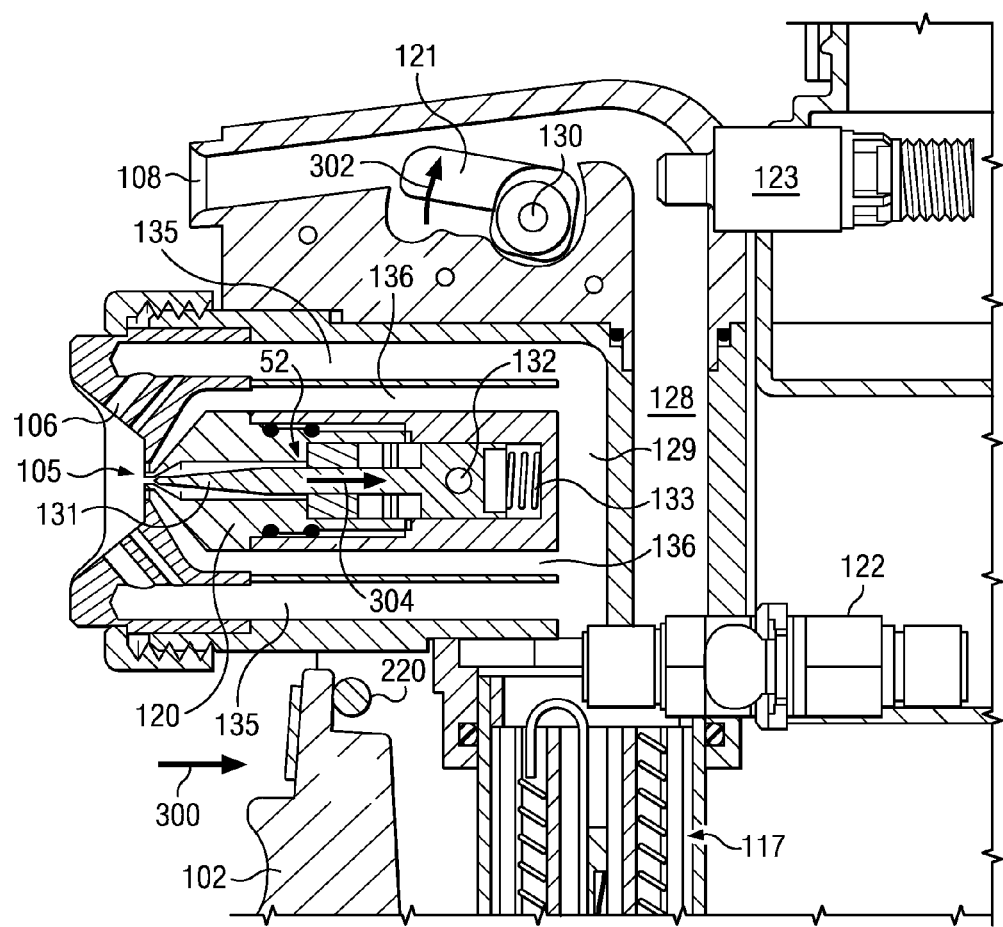
Figure 9C:
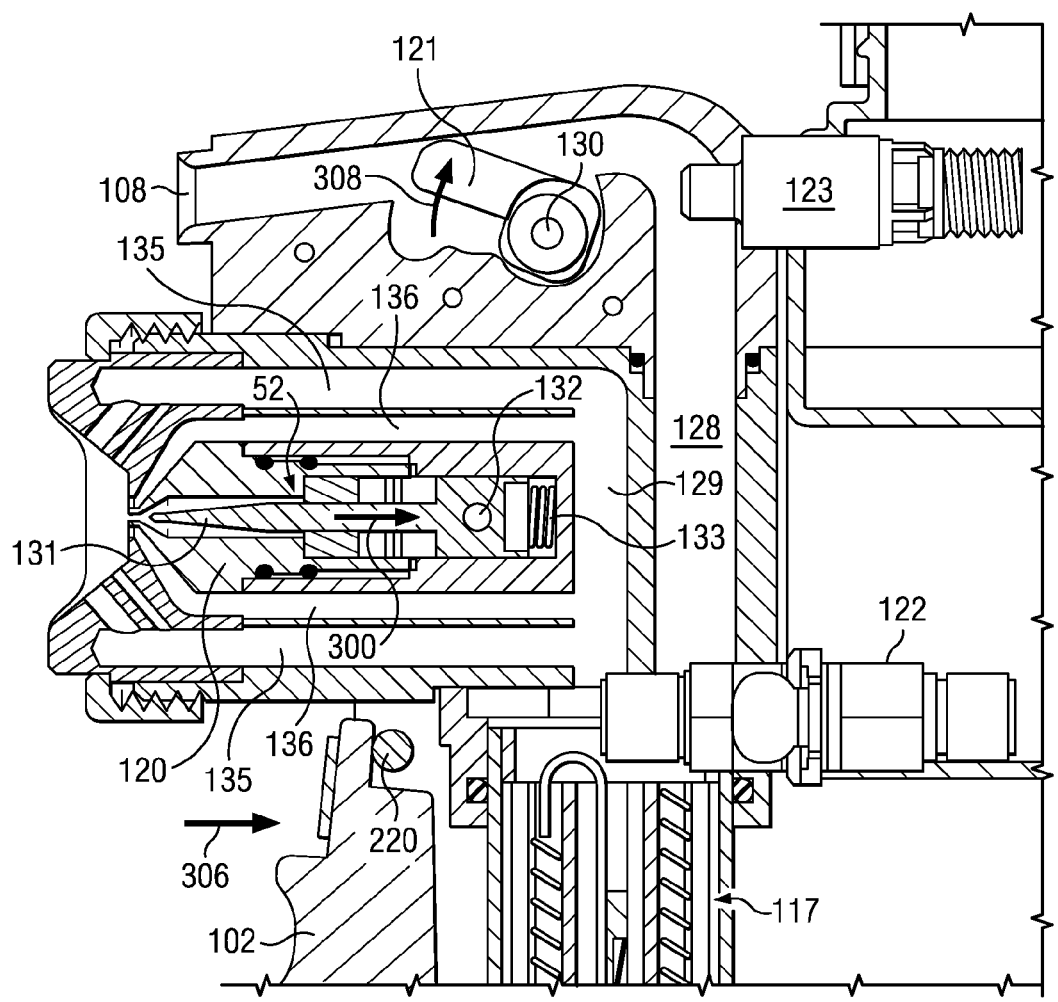

Reference is now made to FIGS. 9A to 9C which illustrate cross sectional views of the hand held sprayer shown in FIG. 6 focusing on the operation of the air and liquid control valves.

Turning first to FIG. 9A, the hand held sprayer is illustrated in an operational configuration where the trigger 102 is fully released. The air valve 121 is in the fully open position, and the liquid valve 52 is in the fully closed position. In this case, pressure is low in the heat port air channel 128 and the liquid supply 110 container is in a relatively low or no pressurized condition (supporting low liquid flow rates to the nozzle). FIG. 9A shows the fluid flow needle 131 of the needle-type liquid control valve 52 positioned within a fluid tip body 120 to fully close the nozzle jet outlet 105. The spring 133 biases the fluid flow needle 131 against the nozzle jet outlet 105 of the fluid tip body 120 in this closed position.

FIG. 9B illustrates that the trigger 102 has been actuated to some degree (as indicated by arrow 300). The air valve 121 has moved to a partially closed position, and the liquid valve 52 has moved to a partially open position. In this case, pressure increases in the heat port air channel 128, air flows through the valve 123 and the liquid supply 110 container is in a relatively medium pressurized condition (supporting medium liquid flow rates to the nozzle). FIG. 9B shows that the flap valve of the air valve 121 has moved (arrow 302) about the pivot 130 to partially close the ducting leading to the heated air outlet 108. FIG. 9B further shows that the fluid flow needle 131 of the needle-type liquid control valve 52 has moved (arrow 304) within the fluid tip body 120 to partially open the nozzle jet outlet 105 (and compress spring 133). The movements 302 and 304 of the flap valve (of the air valve 121) and the fluid flow needle 131 (of the liquid control valve 52) occur in response to actuation of the pin 220 in response to the movement 300 of the trigger 102. The trigger 102 actuates a control linkage mechanism (to be described) of the controller 24 through the pin 220 to move 302 the air valve 121 and move 304 the liquid control valve 52 (through pin 132).

FIG. 9C illustrates that the trigger 102 has been fully actuated (as indicated by arrow 306). The air valve 121 has now moved to a fully closed position, and the liquid valve 52 has moved to a fully open position. In this case, pressure further increases in the heat port air channel 128, air flows through the valve 123 and the liquid supply 110 container is in a relatively high pressurized condition (supporting higher liquid flow rates to the nozzle). FIG. 9C shows that the flap valve of the air valve 121 has moved (arrow 308) about the pivot 130 to fully close the ducting leading to the heated air outlet 108. FIG. 9C further shows that the fluid flow needle 131 of the needle-type liquid control valve 52 has further moved (arrow 310) within a fluid tip body 120 to fully open the nozzle jet outlet 105 (and further compress spring 133). The movement of the flap valve (of the air valve 121) and the fluid flow needle 131 (of the liquid control valve 52) occurs in response to actuation of the pin 220 in response to the movement 302 of the trigger 102. The trigger 102 actuates a control linkage mechanism (to be described) of the controller 24 through the pin 220 to move the air valve 121 and move the liquid control valve 52 (through pin 132).

It will be noted that the fluid tip body 120 is positioned adjacent the atomization air channel 136. As the atomization air channel 136 is coupled to receive heated air from the heating system 117 through the nozzle air channel 129, it will be noted that the heated air will also heat the fluid tip body 120. This advantageously will provide some warming of the spray liquid in the liquid tip at the nozzle jet outlet.

Figure 10A:
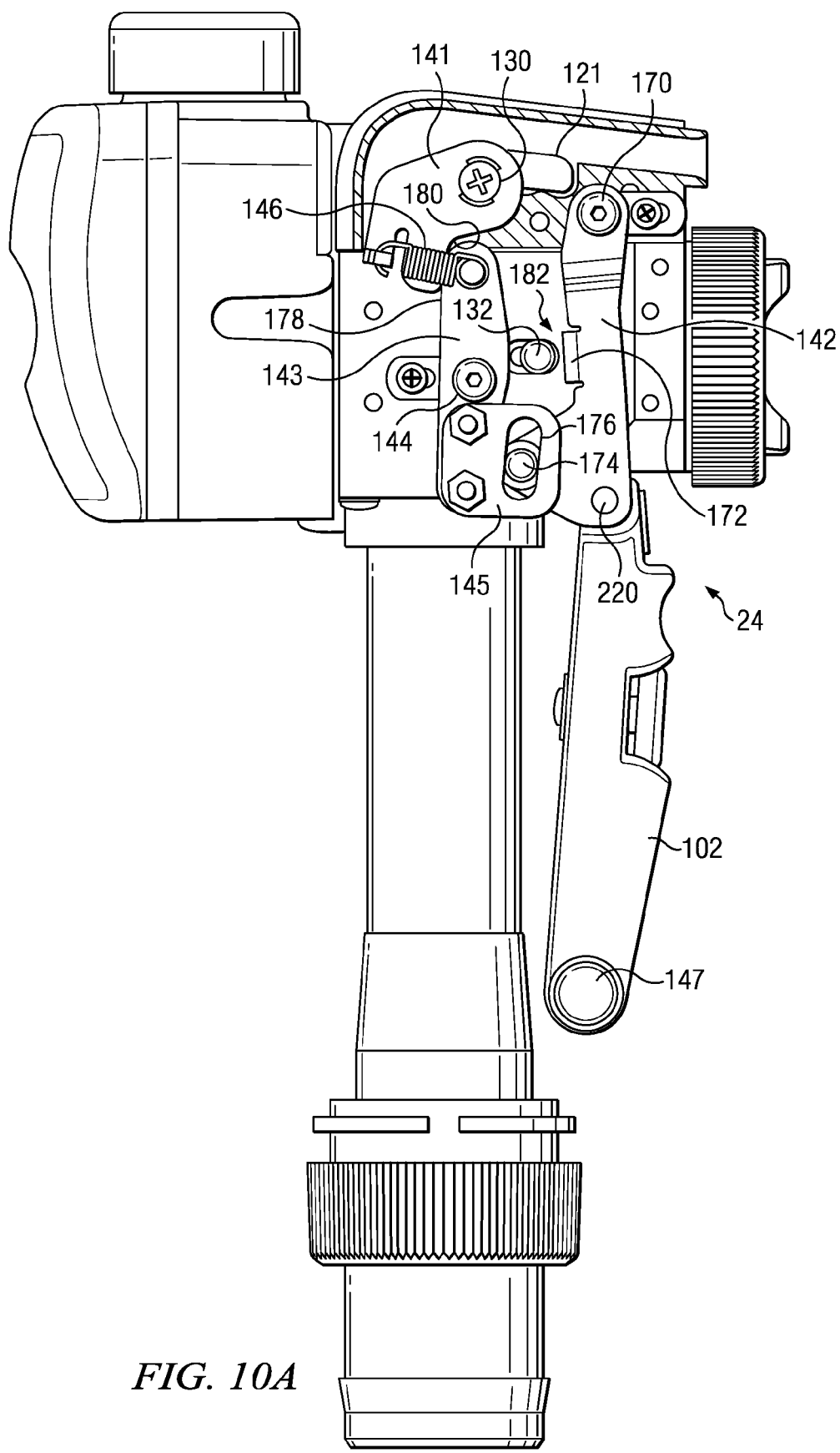
FIGS. 10A to 10C show a mechanical control system for controlling the operation of the air and liquid control valves corresponding to FIGS. 9A-9C.
Figure 10B:
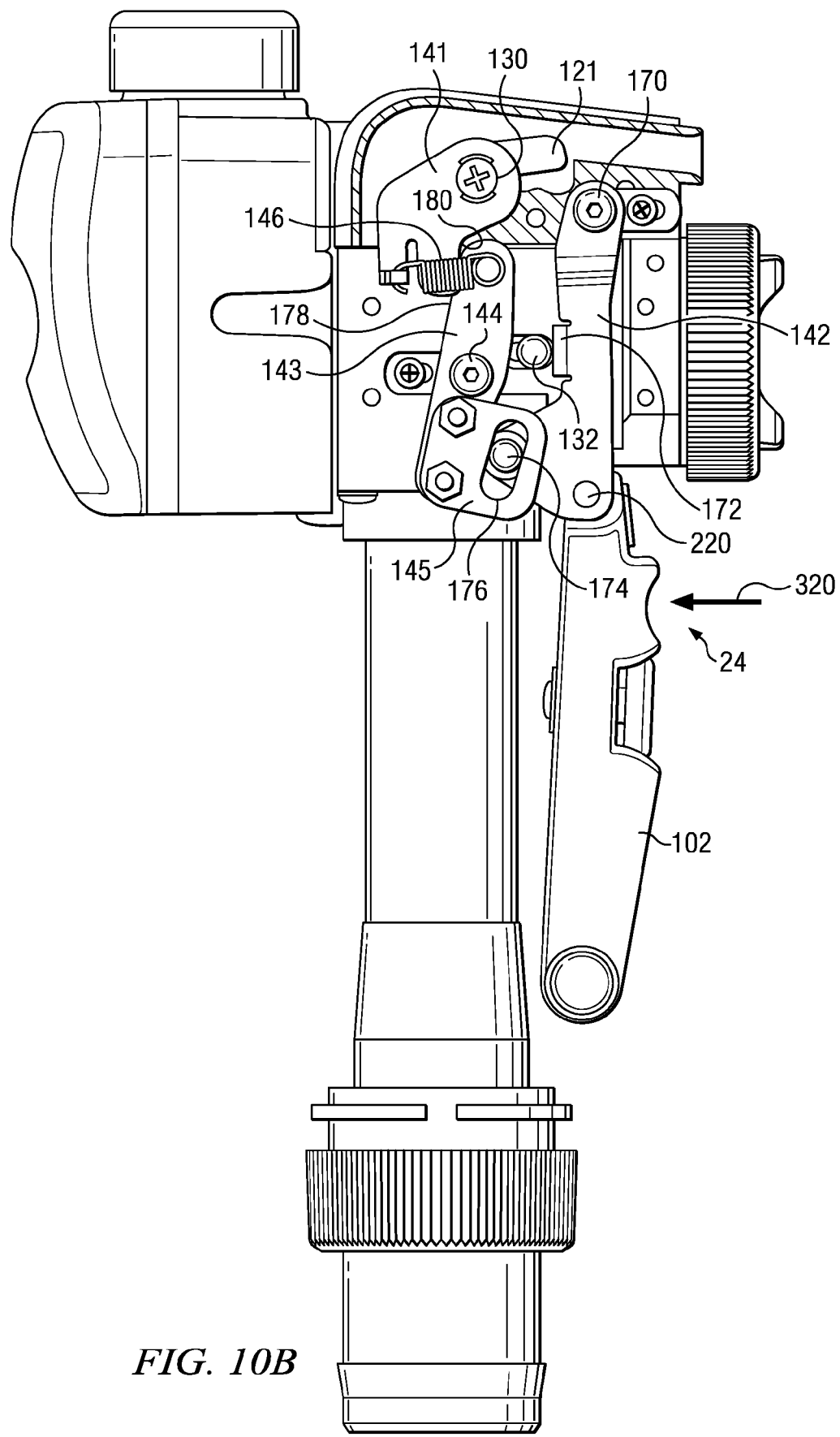
Figure 10C:
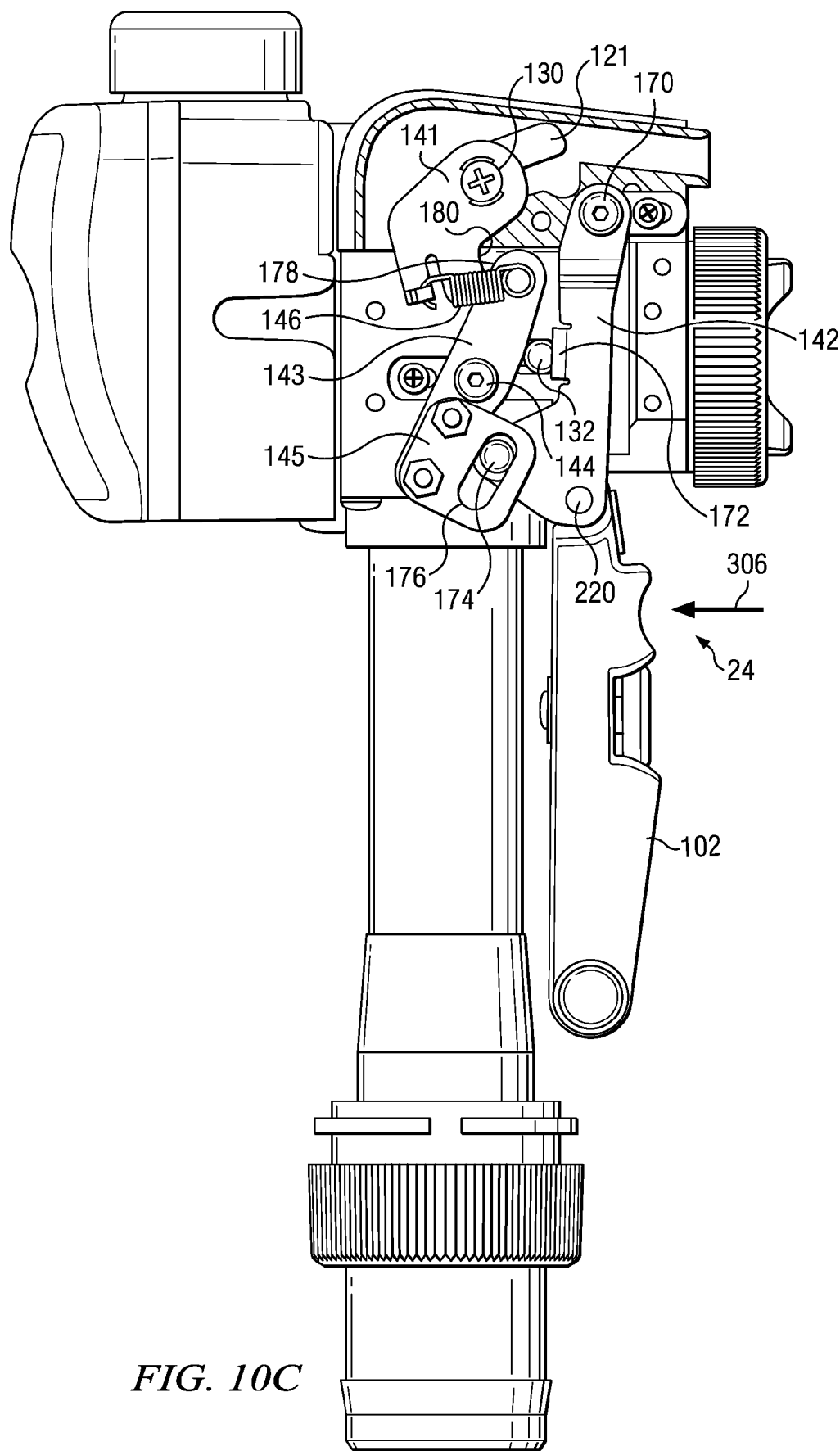
Figure 11:
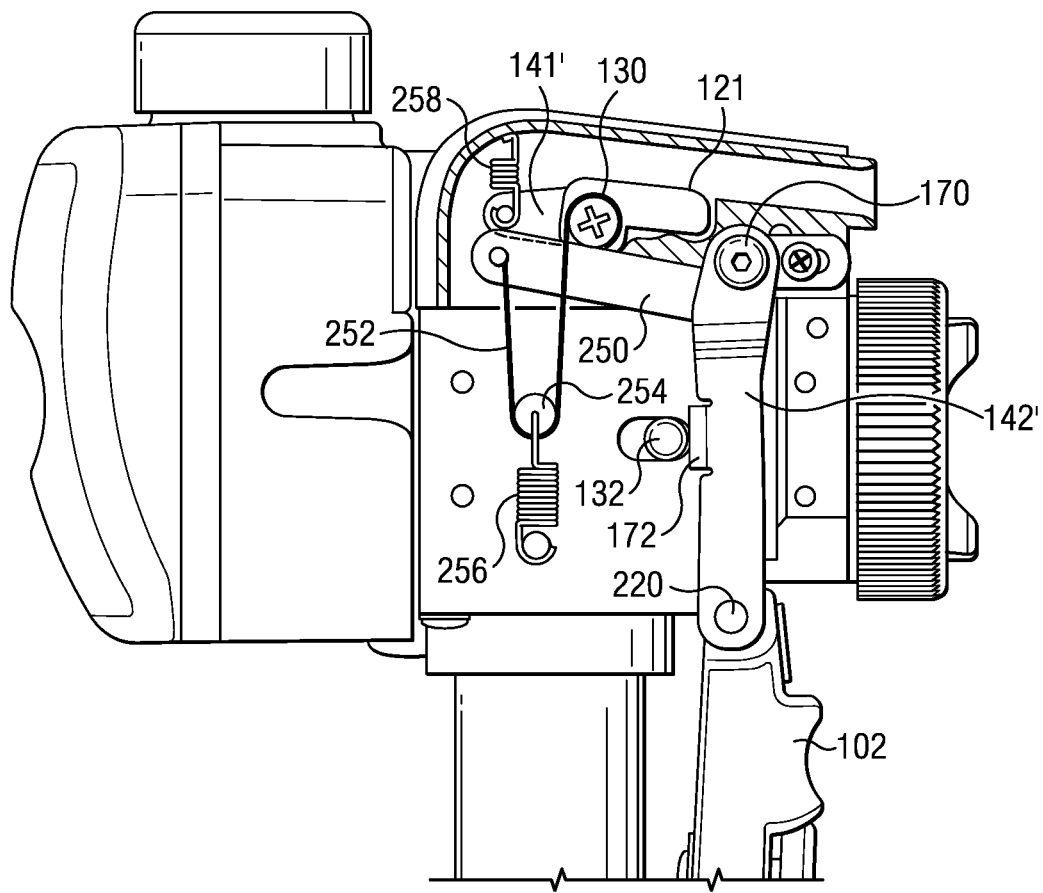
FIG. 11 shows an alternative mechanical control system controlling the operation of the air and liquid control valves corresponding to FIGS. 9A-9C.

As discussed above, the controller 24 may comprise any suitable electrical, mechanical, or electro-mechanical control system that is responsive to user actuation to control operation of the hand held spray member in support of varying operating modes. In the implementation of the hand held sprayer shown in FIGS. 6, 7 and 9A-9C, the controller is has a preferred implementation using a mechanical control system. Reference is made to FIGS. 10A to 10C which show the preferred mechanical control system as well as its operation for controlling the liquid control valve 52 and air valve 121 in the positions shown in FIGS. 9A-9C.

FIG. 10A corresponds to FIG. 9A but shows the mechanical control system of controller 24. The hand held sprayer is illustrated in an operational configuration where the trigger 102 is fully released. As shown, the air valve 121 is in the fully open position. Pin 132 for the needle valve of the liquid valve 52 is shown in a position where the liquid valve 52 will be in the fully closed position (as shown in FIG. 9A where the fluid flow needle 131 of the needle-type liquid control valve 52 positioned within a fluid tip body 120 to fully close the nozzle jet outlet 105).

The mechanical control system for the controller 24 is in the form of a mechanical linkage design (it being understood that such a linkage design is only one example of a mechanical control system and that electrical and electro-mechanical control systems could alternatively be provided). A trigger arm 142 is coupled at a first end to a pivot 170 and at a second end to the pin 220. An actuation pad 172 is provided on the trigger arm 142 approximately midway between the first and second ends and in a position to actuate the pin 132 of the fluid flow needle 131 of the liquid control valve 52. Responsive to actuation of the trigger 102, the trigger arm 142 rotates about pivot 170 and the actuation pad 172 moves into contact with the pin 132. The initial contact of actuation pad 172 with the pin 132 will not cause any change in the liquid control valve 52. However, as the trigger 102 is further actuated, the continued rotation of the trigger arm 142 about pivot 170 will cause a movement of the pin 132. The movement of pin 132 produces a corresponding movement in the fluid flow needle 131 within the fluid tip body 120. This movement compresses the spring 133 and opens the nozzle spray jet outlet 105. When the trigger 102 is released, the spring 133 causes the fluid flow needle 131 to return to its closed position within the fluid tip body 120, and further returns pin 132 to the position shown in FIGS. 9A and 10A.

The trigger arm 142 further includes a pin 174 located near the second end and offset from the pin 220. The pin 174 is positioned within a slot 176 of an actuator cam link 145. The cam link 145 is mounted at a first end of an air valve link actuator 143. The air valve link actuator 143 is mounted for rotation at about its center point to a pivot 144. A second end of the air valve link actuator 143 provides a first valve actuator surface 178. The air valve 121 comprises a vane member and an actuating arm member 141. The vane member and actuating arm member 141 are coupled together and rotate about the pivot 130. The actuating arm member 141 includes second valve actuator surface 180. The first valve actuator surface 178 and second valve actuator surface 180 are not fixedly connected to each other, but rather are positioned to slide relative to each other during movement of the actuating arm member 141 and air valve link actuator 143. A tension spring 146 is provided to couple the second end of the air valve link actuator 143 to the actuating arm member 141 and bias first valve actuator surface 178 and second valve actuator surface 180 in sliding contact with each other.

The tension spring 146 further allows air valve actuator link 143 to continue moving after air valve 121 is fully closed. This is desired to allow liquid valve 52 to open still further in response to trigger 102 actuation and independent of the fully closed position of the air valve 121. In this mode, the second valve actuator surface 180 will separate from first valve actuator surface 178.

Responsive to actuation of the trigger 102, the trigger arm 142 rotates about pivot 170, and the pin 174 actuates the cam 145 by sliding within the slot 176. This causes the air valve link actuator 143 to rotate about pivot 144. The tension spring 146 maintains contact between the first valve actuator surface 178 on the air valve link actuator 143 and the second valve actuator surface 180 of the actuating arm member 141. These surfaces slide against each other as the actuating arm member 141 rotates about pivot 130 in response to the rotation of the air valve link actuator 143. The rotation of the actuating arm member 141 produces a corresponding rotation of the vane member about pivot 130 so as to move the vane of the air valve 121 towards the fully closed position (it being remembered that at the same time the fluid control 52 is moving towards the fully open position). As discussed above, when the trigger 102 is released, the spring 133 will cause the fluid flow needle 131 to return to its closed position within the fluid tip body 120 and return pin 132 to the position shown in FIGS. 9A and 10A. In the absence of any trigger 102 actuation, the heated air flowing past the air valve 121 will push the vane of the air valve 121 towards the fully open position. A return spring (not shown) coupled to trigger arm 142 may also be used to return all linkages to the un-actuated position (see, FIG. 10A). This causes rotation of the actuating arm member 141 about pivot 130. The tension spring 146 coupled the end of actuating arm member 141 will pull on air valve link actuator 143 while the first valve actuator surface 178 on the air valve link actuator 143 slides against the second the second valve actuator surface 180. This produces a rotation of the air valve link actuator 143 about pivot 144. Responsive thereto, the cam 145 and trigger arm 142 are returned to the positions shown in FIGS. 9A and 10A.

It will be noted that there is an offset 182 between the actuation pad 172 of the trigger arm 142 and the pin 132 of the fluid flow needle 131 when the liquid control valve 52 is in the fully closed position and the air valve 121 is in the fully open position (i.e., when the spray device trigger 102 is not actuated as shown in FIG. 9A). The offset 182 permits an initial actuation of the trigger 102 to start closing the air valve 121 before a further actuation of the trigger 102 starts opening the liquid control valve 52. This is illustrated in FIG. 10B. It will be noted that trigger 102 has been partially actuated (arrow 320). The offset 182 (FIG. 10A) has been eliminated and the actuation pad 172 of the trigger arm 142 is now in contact with the pin 132 of the fluid flow needle 131. However, this initial partial trigger 102 actuation 320 has not caused any movement of the pin 132 and thus the liquid control valve 52 remains closed (the fluid flow needle 131 of the needle-type liquid control valve 52 positioned within a fluid tip body 120 to fully close the nozzle jet outlet 105). Notwithstanding the foregoing, however, it will be noted that the configuration of the controller 24 and mechanical linkages has caused the trigger arm 142 to rotate about pivot 170, the pin 174 to actuate the cam 145 by sliding within the slot 176, the air valve link actuator 143 to rotate about pivot 144, the first valve actuator surface 178 on the air valve link actuator 143 to slide with respect to the second valve actuator surface 180, and the actuating arm member 141 to rotates about pivot 130 in response to tension spring 145 so as to move the vane member and partially close the air valve 121.

With reference once again to FIG. 9A, the foregoing operation to partially close the air valve 121 prior to any action to open the liquid control valve 52 is advantageous because the partial closure of the air valve 121 will raise the air pressure within at least the nozzle air channel 129. An elevation in air pressure within the nozzle air channel 129 produces an increased air flow rate through the pattern shaping air channel 135 to the pattern shaping air port 108 and atomization air channel 136 to the air atomization port 91. Then, as shown in FIG. 9B, when the fluid flow needle 131 of the needle-type liquid control valve 52 does move 304 to partially open the nozzle jet outlet 105, a suitable air flow at both the pattern shaping air port 108 and air atomization port 91 is present to generate the spray cloud. FIG. 10B shows the linkage position in response to the initial actuation of the trigger 102 just prior to the further actuation 300 of the trigger 102 in FIG. 9B to partially open the liquid control valve 52.

FIG. 10C corresponds to FIG. 9C. The hand held sprayer is illustrated in an operational configuration where the trigger 102 has been fully actuated. As shown, the air valve 121 has moved to the fully closed position. Pin 132 for the needle valve of the liquid valve 52 is shown to have moved to a position where the liquid valve 52 will be in the fully open position (as shown in FIG. 9C where the fluid flow needle 131 of the needle-type liquid control valve 52 positioned within a fluid tip body 120 to fully open the nozzle jet outlet 105).

The linkage configuration of FIGS. 10A to 10C represents one possible mechanical configuration. A different mechanical configuration is shown in FIG. 11 which utilizes a cable and string operation. A trigger arm 142' is coupled at a first end to a pivot 170 and at a second end to the pin 220. An actuation pad 172 is provided on the trigger arm 142' approximately midway between the first and second ends and in a position to actuate the pin 132 of the fluid flow needle 131 of the liquid control valve 52. Responsive to actuation of the trigger 102, the trigger arm 142' rotates about pivot 170 and the actuation pad 172 moves into contact with the pin 132. The initial contact of actuation pad 172 with the pin 132 will not cause any change in the liquid control valve 52. However, as the trigger 102 is further actuated, the continued rotation of the trigger arm 142' about pivot 170 will cause a movement of the pin 132. The movement of pin 132 produces a corresponding movement in the fluid flow needle 131 within the fluid tip body 120. This movement compresses the spring 133 and opens the nozzle spray jet outlet 105. When the trigger 102 is released, the spring 133 causes the fluid flow needle 131 to return to its closed position within the fluid tip body 120, and further returns pin 132 to the position shown in FIG. 11.

The trigger arm 142' includes an extending member 250 which extends from approximately the first end in a perpendicular direction. A cable 252 is connected at the distal end of the extending member 250. The cable 252 wraps around a pulley 254 that is coupled to a fixed point by a tension spring 256. The air valve 121 comprises a vane member and an actuating arm member 141'. The vane member and actuating arm member 141' are coupled together and rotate about the pivot 130. After wrapping around the pulley 254, the cable 252 is further wrapped around the pivot 130 and connected to the vane of the air valve 121. A return spring 258 is coupled to the end of the actuating arm member 141'.

Responsive to actuation of the trigger 102, the trigger arm 142' rotates about pivot 170, and the extending member 250 pulls up on cable 252. The movement is translated by the pulley 254 into a downward force on cable 252 with respect to the pivot 130 resulting in a rotation of the vane member and actuating arm member 141' about pivot 130, a tensioning of spring 258 and a closing of the air valve 121. When the trigger 102 is released, the spring 258 pulls on actuating arm member 141' causing a rotation about the pivot 130 and the opening of the air valve 121. Tension on the cable 252 reverses direction and the mechanical configuration returns to the position shown in FIG. 11.

The system 10 supports a controlled spraying and drying operation. This operation includes using the hand held spray member and the heated air stream 37 in one or more passes over the skin of the customer. This heated air treatment serves one primary purpose of warming the skin of the customer in anticipation of a subsequent liquid spraying. Next, the hand held spray member with the jet outlet 105 and air outlet 108 is used in one or more passes to spray a skin treatment liquid over the customer's skin. The heated air stream 37 in this step is used to warm the spray cloud 33 produced by the nozzle 104. More particularly, the heated air stream 37 is directed at the leading edge of the spray cloud 33 as the hand held spray member moves along the customer's skin and applies the liquid. A heated air stream 37 may additionally be directed at the trailing edge of the spray cloud to initiate a drying of the skin surface. Last, the hand held spray member and the heated air stream 37 alone is used in one or more passes over the skin of the customer. This heated air treatment serves two purposes: a) it dries the skin quickly after spraying which has been shown to enhance the end result of the spraying; and b) it keeps the customer warm (perhaps in anticipation of a subsequent spraying). The foregoing operations may then be repeated for those applications which require multiple spray passes (such as to provided thicker coverage or to change liquid application).

The system 10 described herein supports exercising control over the operation of the heated air flow, heat levels, nozzle operation, liquid selection, and nozzle movement. An exemplary sequence of operations comprises: pre-heating of spray area (target) with heated air; application of a first spray solution (with or without heated air); a drying cycle using heated air application; application of a second spray solution (with or without heated air); a drying cycle using heated air application; application of a third spray solution (with or without heated air); and a final drying cycle using heated air application. Another exemplary sequence of operations comprises: pre-heating of spray area with heated air; first pass application of a first spray solution (with or without heated air); a drying cycle using heated air application; second pass application of the same first spray solution (with or without heated air); a drying cycle using heated air application; first pass application of a second spray solution (with or without heated air); a drying cycle using heated air application; second pass application of the same second spray solution (with or without heated air); and a final drying cycle using heated air application.

Improved results using the apparatus and process described herein, with a trial using DHA (dihydroxyacetone) based sunless tanning compounds, include:

Increased tan color by allowing higher quantities of sprayed active ingredient to be deposited due to a layering process where the spray is applied; the skin is re-dried quickly by the warm air flow before another spray pass over the same target area;

Promotes deeper activity of DHA by drying the top layer of skin completely and possibly by drying inner layers of the stratum corneum skin layer; this results in longer lasting tan color;

Opens skin surface pores to allow for better penetration of tanning compound and skin care ingredients;

Properly controlled heated air dries the skin of any perspiration or other moisture, including the water based spray itself, that may cause an uneven tanning effect and prevent penetration into skin layers;

Prevents dripping or streaking of the sprayed material during the tanning process which can cause an uneven tanning result; and Eliminates the step of drying the skin off with a towel which causes partial removal and disturbance of the evenly deposited layer from the spray application.

Although preferred embodiments of the method and apparatus of the present invention have been illustrated in the accompanying Drawings and described in the foregoing Detailed Description, it will be understood that the invention is not limited to the embodiments disclosed, but is capable of numerous rearrangements, modifications and substitutions without departing from the spirit of the invention as set forth and defined by the following claims.

The invention claimed is:

1. Apparatus, comprising:
a hand held spray member;
a spray nozzle supported by the hand held spray member, the spray nozzle including a spray jet outlet adapted to spray a human skin treatment liquid from the spray nozzle and produce an atomized spray cloud of the human skin treatment liquid;
a liquid valve supported by the hand held spray member, the liquid valve adapted to control flow of the human skin treatment liquid to the spray jet outlet;
a warm air outlet separate from the spray jet outlet, the warm air outlet adapted to deliver heated air in a warm air stream directed to mix with and warm the atomized spray cloud produced by the spray jet outlet;
an air valve supported by the hand held spray member, the air valve adapted to control flow of air to the warm air outlet; and
a controller adapted to control actuation of the liquid valve and air valve in response to a triggering actuation, wherein the control actuation implemented by the controller comprises moving the air valve towards close while moving the liquid valve towards open in response to the triggering actuation.

2. The apparatus of claim 1, wherein the control actuation implemented by the controller further comprises partially closing the air valve in response to the triggering actuation prior to opening the liquid valve.

3. The apparatus of claim 1, wherein the control actuation implemented by the controller further comprises partially closing the air valve while partially opening the liquid valve in response to the triggering actuation.

4. The apparatus of claim 1, wherein the air valve is a flap valve.

5. The apparatus of claim 1, wherein the air valve is a spool valve.

6. The apparatus of claim 1, wherein the liquid valve is a needle valve.

7. The apparatus of claim 1, further comprising a heating unit supported by the hand held spray member and adapted to heat the air delivered to the warm air outlet for the warm air stream.

8. The apparatus of claim 7, wherein the spray jet outlet is adapted to spray the human skin treatment liquid along a first trajectory and the warm air outlet is adapted to deliver the heated air in the warm air stream along a second trajectory, further wherein the first and second trajectories intersect each other such that the heated air in the warm air stream mixes with the atomized spray cloud.

9. The apparatus of claim 7, wherein the spray jet outlet of the spray nozzle induces a drop in temperature of the human skin treatment liquid within the atomized spray cloud due to a nozzle expansion effect, and wherein the warm air stream directed to mix with the atomized spray cloud counteracts the induced drop in temperature.

10. The apparatus of claim 1, wherein the spray nozzle is an air-assisted atomizing type nozzle including at least one atomizing air port, and wherein the heated air is also supplied to the atomizing air port of the air-assisted atomizing type nozzle for use in atomizing the human skin treatment liquid at the spray jet outlet.

11. The apparatus of claim 10, wherein closure of the air valve increases pressure of the heated air for use at the atomizing air port in atomizing the human skin treatment liquid at the spray jet outlet.

12. The apparatus of claim 11, wherein the actuation controlled by the controller comprises proportionally closing the air valve while proportionally opening the liquid valve.

13. The apparatus of claim 10, wherein the air valve is adapted to selectively direct the heated air towards one or both of the atomizing air port of the air-assisted atomizing type nozzle and the warm air outlet.

14. The apparatus of claim 1, further including a container adapted to hold the human skin treatment liquid, wherein the container is supported by the hand held spray member, and further including a pressurization valve coupled to receive air to pressurize the container.

15. The apparatus of claim 14, wherein closure of the air valve increases pressure of the air for use pressurizing the container.

16. The apparatus of claim 14, wherein the container is detachably connected to a housing of the hand held spray member.

17. The apparatus of claim 1, wherein the controller comprises a mechanical linkage coupling the trigger actuation to the liquid valve and the air valve.

18. The apparatus of claim 1, further including means for imparting an electrostatic charge on the atomized spray cloud.

19. The apparatus of claim 1, wherein the warm air outlet is further adapted to deliver heated air in the warm air stream directed to shape a spray pattern of the atomized spray cloud produced by the spray jet outlet.

20. The apparatus of claim 1, further comprising:
a housing for the hand held spray member including a handle portion; and
a heating unit positioned within the handle portion and adapted to heat the air delivered to the warm air outlet for the warm air stream.

21. The apparatus of claim 1, wherein the control actuation implemented by the controller supports a plurality of operating modes including:
a first mode wherein the liquid valve is closed and the air valve is open;
a second mode wherein the liquid valve is partially open and the air valve is partially closed; and
a third mode wherein the liquid valve is open and the air valve is closed.

22. The apparatus of claim 1, wherein the control actuation implemented by the controller supports a plurality of operating modes including:
a first mode wherein the liquid valve is closed and the air valve is open;
a second mode wherein the liquid valve is closed and the air valve is partially closed;
a third mode wherein the liquid valve is partially open and the air valve is partially closed; and
a fourth mode wherein the liquid valve is open and the air valve is closed.

23. The apparatus of claim 1 wherein the heated air further heats the human skin treatment liquid at the nozzle.

24. Apparatus, comprising:
a hand held spray member;
a spray nozzle supported by the hand held spray member, the spray nozzle including a spray jet outlet adapted to spray a human skin treatment liquid from the spray nozzle and produce an atomized spray cloud of the human skin treatment liquid;
a liquid valve supported by the hand held spray member, the liquid valve adapted to control flow of the human skin treatment liquid to the spray jet outlet;
a warm air outlet separate from the spray jet outlet, the warm air outlet adapted to deliver heated air in a warm air stream directed to mix with and warm the atomized spray cloud produced by the spray jet outlet;
an air valve supported by the hand held spray member, the air valve adapted to control flow of air to the warm air outlet;
a controller adapted to control actuation of the liquid valve and air valve in response to a triggering actuation; and
means for ionizing the air in the warm air stream.

25. Apparatus, comprising:
a hand held spray member;
a spray nozzle supported by the hand held spray member, the spray nozzle including a spray jet outlet adapted to spray a human skin treatment liquid from the spray nozzle and produce an atomized spray cloud of the human skin treatment liquid;
a liquid valve supported by the hand held spray member, the liquid valve adapted to control flow of the human skin treatment liquid to the spray jet outlet;
a warm air outlet separate from the spray jet outlet, the warm air outlet adapted to deliver heated air in a warm air stream directed to mix with and warm the atomized spray cloud produced by the spray jet outlet;
an air valve supported by the hand held spray member, the air valve adapted to control flow of air to the warm air outlet; and
a controller adapted to proportionally control opening and closing of the liquid and air valves,
wherein the proportional control comprises an inversely proportional control of opening and closing of the liquid and air valves,
wherein the spray nozzle is an air-assisted nozzle including an atomizing air outlet, and
wherein the controller operates responsive to a triggering actuation to proportionally divide air between the warm air outlet and the atomizing air outlet.

26. The apparatus of claim 25, further comprising a trigger supported by the hand held spray member, wherein the controller operates responsive to actuation of the trigger to control opening and closing of the liquid and air valves.

27. Apparatus, comprising:
a hand held spray member;
a spray nozzle supported by the hand held spray member, the spray nozzle including a spray jet outlet adapted to spray a human skin treatment liquid from the spray nozzle and produce an atomized spray cloud of the human skin treatment liquid;
a liquid valve supported by the hand held spray member, the liquid valve adapted to control flow of the human skin treatment liquid to the spray jet outlet;
a warm air outlet separate from the spray jet outlet, the warm air outlet adapted to deliver heated air in a warm air stream directed to mix with and warm the atomized spray cloud produced by the spray jet outlet;
an air valve supported by the hand held spray member, the air valve adapted to control flow of air to the warm air outlet; and
a controller adapted to control operation of the apparatus;
wherein the spray nozzle is an air-assisted nozzle including an atomizing air outlet, and
wherein the controller operates responsive to a triggering actuation to control the air valve so as to reduce air flow at the warm air outlet and increase air flow at the atomizing air outlet.

28. The apparatus of claim 27, wherein the controller further operates responsive to an initial triggering actuation to control the air valve to reduce air flow at the warm air outlet before controlling the liquid valve to increase liquid flow to the nozzle.

29. The apparatus of claim 28, wherein the controller further operates responsive to further triggering actuation to control the air valve to further reduce air flow at the warm air outlet while controlling the liquid valve to increase liquid flow to the nozzle.

30. The apparatus of claim 28, wherein the controller further operates responsive to still further triggering actuation to control the air valve to block air flow at the warm air outlet while controlling the liquid valve to further increase liquid flow to the nozzle.

* * * * *